United States Patent
Cornblatt et al.

(10) Patent No.: US 12,064,471 B2
(45) Date of Patent: *Aug. 20, 2024

(54) COMPOSITIONS COMPRISING SULFORAPHANE OR A SULFORAPHANE PRECURSOR AND A MUSHROOM EXTRACT OR POWDER

(71) Applicant: NUTRAMAX LABORATORIES, INC., Lancaster, SC (US)

(72) Inventors: Brian Cornblatt, Westminster, MD (US); Grace Cornblatt, Westminster, MD (US); Anton Bzhelyansky, Baltimore, MD (US); Robert Henderson, Street, MD (US)

(73) Assignee: NUTRAMAX LABORATORIES, INC., Lancaster, SC (US)

( * ) Notice: Subject to any disclaimer, the term of this patent is extended or adjusted under 35 U.S.C. 154(b) by 246 days.

This patent is subject to a terminal disclaimer.

(21) Appl. No.: 17/178,664

(22) Filed: Feb. 18, 2021

(65) Prior Publication Data

US 2021/0169997 A1 Jun. 10, 2021

Related U.S. Application Data

(63) Continuation of application No. 14/412,191, filed as application No. PCT/US2013/049248 on Jul. 3, 2013, now Pat. No. 10,960,057.

(60) Provisional application No. 61/794,417, filed on Mar. 15, 2013, provisional application No. 61/668,342, filed on Jul. 5, 2012, provisional application No. 61/668,386, filed on Jul. 5, 2012, provisional application No. 61/668,396, filed on Jul. 5, 2012, provisional application No. 61/668,364, filed on Jul. 5, 2012, provisional application No. 61/668,374, filed (Continued)

(51) Int. Cl.

| | |
|---|---|
| A23L 33/105 | (2016.01) |
| A61K 9/00 | (2006.01) |
| A61K 9/14 | (2006.01) |
| A61K 9/28 | (2006.01) |
| A61K 31/19 | (2006.01) |
| A61K 31/194 | (2006.01) |
| A61K 31/26 | (2006.01) |
| A61K 31/357 | (2006.01) |
| A61K 31/375 | (2006.01) |
| A61K 31/7028 | (2006.01) |
| A61K 31/716 | (2006.01) |
| A61K 33/06 | (2006.01) |
| A61K 36/00 | (2006.01) |
| A61K 36/06 | (2006.01) |
| A61K 36/07 | (2006.01) |
| A61K 36/28 | (2006.01) |
| A61K 36/31 | (2006.01) |
| A61K 38/47 | (2006.01) |
| A61K 45/06 | (2006.01) |
| A61K 47/42 | (2017.01) |
| A61P 3/06 | (2006.01) |

(52) U.S. Cl.
CPC ............ *A61K 38/47* (2013.01); *A23L 33/105* (2016.08); *A61K 9/0053* (2013.01); *A61K 9/14* (2013.01); *A61K 9/28* (2013.01); *A61K 31/19* (2013.01); *A61K 31/194* (2013.01); *A61K 31/26* (2013.01); *A61K 31/357* (2013.01); *A61K 31/375* (2013.01); *A61K 31/7028* (2013.01); *A61K 31/716* (2013.01); *A61K 33/06* (2013.01); *A61K 36/06* (2013.01); *A61K 36/07* (2013.01); *A61K 36/28* (2013.01); *A61K 36/31* (2013.01); *A61K 45/06* (2013.01); *A61K 47/42* (2013.01); *A61P 3/06* (2018.01); *C12Y 302/01147* (2013.01); *A23V 2002/00* (2013.01)

(58) Field of Classification Search
None
See application file for complete search history.

(56) References Cited

U.S. PATENT DOCUMENTS

| 5,607,677 A | 3/1997 | Jamas et al. |
|---|---|---|
| 7,923,044 B2 | 4/2011 | Bias |

(Continued)

FOREIGN PATENT DOCUMENTS

| CN | 1149986 A | 5/1997 |
|---|---|---|
| CN | 101514174 A | 8/2009 |

(Continued)

OTHER PUBLICATIONS

Australian Government IP Australia, Examination Report No. 1 for standard patent application No. 2020217440, report date Aug. 30, 2021, 6 pages.

(Continued)

*Primary Examiner* — Aaron J Kosar
*Assistant Examiner* — Randall O Winston
(74) *Attorney, Agent, or Firm* — Dickinson Wright PLLC

(57) ABSTRACT

The present disclosure relates to the synergistic combination of a sulforaphane precursor, an enzyme capable of converting the sulforaphane precursor to sulforaphane, a cofactor of the enzyme, and a glucan. The present disclosure also relates to the synergistic combination of sulforaphane or a derivative thereof and a glucan. The present disclosure also relates to the synergistic combination of a broccoli extract or powder and a glucan. The glucan may be a β-glucan. The glucan may be provided in a mushroom extract or powder selected from one or more of a maitake, a shiitake, or a reishi mushroom. Compositions and methods relating to these combinations are described.

32 Claims, 6 Drawing Sheets

Related U.S. Application Data on Jul. 5, 2012, provisional application No. 61/668,328, filed on Jul. 5, 2012.

(56) References Cited

U.S. PATENT DOCUMENTS

| | | | |
|---|---|---|---|
| 9,421,183 | B2 | 8/2016 | Cornblatt et al. |
| 10,583,178 | B2 | 3/2020 | Cornblatt et al. |
| 10,960,057 | B2* | 3/2021 | Cornblatt ............ A61K 31/7028 |
| 2003/0091518 | A1 | 5/2003 | Pauly et al. |
| 2006/0264497 | A1* | 11/2006 | Zeligs ................. A61K 31/404 |
| | | | 514/414 |
| 2008/0311192 | A1 | 12/2008 | West et al. |
| 2009/0252796 | A1* | 10/2009 | Mazed ................... A61K 36/54 |
| | | | 424/490 |
| 2010/0015109 | A1 | 1/2010 | Bias |
| 2011/0014137 | A1 | 1/2011 | Talalay et al. |
| 2011/0206721 | A1* | 8/2011 | Nair ........................ A61P 29/00 |
| | | | 424/195.15 |
| 2011/0262595 | A1 | 10/2011 | Lee |
| 2015/0110872 | A1 | 4/2015 | Cornblatt et al. |
| 2015/0147352 | A1 | 5/2015 | Cornblatt et al. |
| 2020/0101143 | A1 | 4/2020 | Cornblatt et al. |
| 2021/0169997 | A1 | 6/2021 | Cornblatt et al. |

FOREIGN PATENT DOCUMENTS

| | | |
|---|---|---|
| CN | 101553134 A | 10/2009 |
| CN | 102450534 A | 5/2012 |
| CN | 102526455 A | 7/2012 |
| DE | 102010022587 A1 | 12/2011 |
| JP | H07252148 A | 10/1995 |
| JP | 2002191323 A | 7/2002 |
| JP | 2005073508 A | 3/2005 |
| JP | 2005341964 A | 12/2005 |
| JP | 2007320947 A1 | 12/2007 |
| JP | 2010259424 A | 11/2010 |
| JP | 2011500680 A | 1/2011 |
| JP | 6548573 B2 | 7/2019 |
| KR | 20080030722 A | 4/2008 |
| KR | 20100016876 A | 2/2010 |
| KR | 101079643 B1 | 11/2011 |
| RU | 2292899 C2 | 1/2006 |
| RU | 2319494 C2 | 3/2008 |
| WO | 0007607 A1 | 2/2002 |
| WO | 2008002175 A1 | 3/2008 |
| WO | 2008115583 A1 | 9/2008 |
| WO | 2009051739 A1 | 4/2009 |
| WO | 2011060585 A1 | 5/2011 |
| WO | 2011106417 A1 | 9/2011 |
| WO | 2012074412 A1 | 6/2012 |
| WO | 2012122295 A2 | 9/2012 |
| WO | 2014008353 A2 | 1/2014 |

OTHER PUBLICATIONS

Decision to Grant a Patent with English translation mailed Jan. 31, 2023 for Japanese Application No. 2020-196733, 8 pages.
Japanese Office Action mailed Nov. 22, 2022 for Japanese Application No. 2020-196733, 1 page.
Akinon Yanaka et al, English Abstract for "Daily Intake of Sulforaphane-Rich Broccoli Sprouts Suppresses H. pyloriColonization and Attenuates H.pylori-induced Gastritis via Upregulation of Nrf2-dependent Antixodaint Enzymes", Japan Complementary Alternative Medicine Journal, 2007, vol. 4, No. 1, pp. 9-15.
Albena T. Dinkova-Kostova et al, "NAD(P)H:quinone acceptor oxidoreductase 1 (NQOI), a multifunctional antioxidant enzyme and exceptionally versatile cytoprotector", Archives of Biochemistry and Biophysics, 2010, vol. 501, pp. 116-123.
"Antioxident properties of green broccoli and purple-sprouting broccoli under different cooking conditions". Bioscience Horizons, May 7, 2012, vol. 5, pp. 1-11, DOI: 10.1093/biohprozons/hzs004.
Liam Baird et al, "The cytoprotective role of the Keap1-Nrf2 pathway", Arch Toxicol, 2011, vol. 85, pp. 241-272.
Zaidman, Ben-Zion et al, "Medicinal mushroom modulators of molecular targets as cancer therapeutics", Applied Microbiology and Biotechnology, (2005) , pp. 453-468.
Cornblatt, Brian S. et al, "Preclinical and clinical evaluation of sulforaphane for chemoprevention in the breast", Carcinogenesis, 2007, vol. 28(7), pp. 1485-1490, Epub Mar. 7, 2007.
Egilius L. H. Spierings et al, "A Phase I Study of the Safety of the Nutritional Supplement, Active Hexose Correlated Compound, AHCC, in Healthy Volunteers", J. Nutr Sci Vitaminol, 2007, vol. 53, pp. 536-539.
Isieh, Tze-Chen et al, "Suppression of proliferation and oxidative stress by extracts of Ganoderma lucidum in the ovarian cancer cell line OVCAR-3", International Journal of Molecular Medicine, 2011, vol. 28, pp. 1065-1069.
James, Don et al, "Novel concepts of broccoli sulforaphanes and disease: induction of phase II antioxidant and detoxification enzymes by enhanced-glucoraphanin broccoli", Nutrition Review, 2012, vol. 70(11), pp. 654-665.
Ji Yu-Bin, et al., English Abstract for Study on extraction, isolation and anticarcinogenic activity of sulforaphane in broccoli. Journal of Harbin University of Commerce (Natural Sciences Edition), vol. 21, No. 3, pp. 270-273—Jun. 30, 2005.
Kun Hu et al, "Synthesis and biological evaluation of sulforaphane derivatives as potential antitumor agents", European Journal of Medicinal Chemistry, 2013, vol. 64, pp. 529-539.
Liu, Ann G. et al, "Feeding Tomato and Broccoli Powders Enriched with Bioactives Improves Bioactivity Markers in Rats", JAgric Fppd Chem, 2009, vol. 57(16), pp. 7304-7310.
Masaru Ohtsuru et al, "The Interaction of L•Ascorbic Acid With the Active Center of Myrosinase", Biochemica et Biophysica Acta,m 1979, vol. 567. pp. 384-391.
Driscoll, Michael et al, "Therapeutic potential of various beta-glucan sources in conjunction with anti-tumor monoclonal antibody in cancer therapy", Cancer Biology & Therapy 803, 2009, pp. 218-225.
Okic-Djordjevic, I., et al, "GE132+ Natural: Novel promising dietetic supplement with antiproliferative influence on prostate, colon, and breast cancer cells", JBUON, 2013, vol. 18(2), pp. 504-510.
Shankar, Sharmila et al, "Sulforaphane Enhances the Therapeutic Potential of TRAIL in Prostate Cancer Orthotopic Model through Regulation of Apoptosis, Metastasis, and Angiogenesis", Clinical Cancer Research 14.21, 2008, pp. 6855-6866.
Shapiro, Theresa et al, "Human Metabolism and Excretion of Cancer Chemoprotective Glucosinolates and Isothiocyanates of Cruciferous Vegetables, Cancer Epidemiology, Biomarkers & Prevention", Dec. 1998, pp. 1091-1100, vol. 7.
Su Guangyao, et al. English Ab stract for "Enzymatic Hydrolysis Conditions of Glucosinolate in Broccoli Seeds". Journal of the Chinese Cereals and Oils Association, vol. 23, No. 2, pp. 178-182— Mar. 31, 2008.
Sunan, Wang et al, "Synergistic, Additive, and Antagonistic Effects of Food Mixtures on Total Antioxidant Capacities", J. Agric. Food Chem., 2011, vol. 59 pp. 960-968.
Vallejo, Fernando et al, "Potential bioactive compounds in health promotion from broccoli cultivars grown in Spain", J. Sci. Food Agric, 2002, vol. 82, pp. 1293-1297.
Yanyan,Li et al, "Sulforaphane, a Dietary Component of Broccoli/Broccoli Sprouts, Inhibits Breast Cancer Stem Cells", Clin Cancer Res, May 2010, vol. 16, No. 9, pp. 2580-2590.
Yasujiro Morimitsu et al, "A Sulforaphane Analogue That Potently Activates the Nrf2-dependent Detoxification Pathway", The Journal of Biological Chemistry, vol. 277, No. 5, 2002, pp. 3456-3464.
Young-Hoon Ahn et al, "Electrophilic tuning of the chemoprotective natural product sulforaphane" PNAS, 2010, vol. 07 (21), pp. 9590-9595.
English Abstract for WO2011060585A1 dated May 26, 2011.
English Abstract for KR20100016876A dated Feb. 16, 2010.
English Abstract for JP2007320947A dated Dec. 13, 2007.
English Abstract for JP2005341964A dated Dec. 15, 2005.
English Abstract for JPH07252148A dated Oct. 3, 1995.
English Abstract for DE102010022587A1 dated Dec. 1, 2011.

(56) References Cited

OTHER PUBLICATIONS

English Abstract for RU2292899C2 dated Jan. 10, 2006.
English Abstract for RU2319494C2 dated Mar. 20, 2008.
English Abstract for WO2008002175A1 dated Mar. 1, 2008.
English Abstract for JP2010259424A dated Nov. 18, 2010.
English Abstract for JP2015523366 dated Aug. 13, 2015.
English Abstract for KR101079643B1 dated Nov. 4, 2011.
English Abstract Translation for CN102450534A dated May 16, 2012.
English Abstract Translation for CN1149986A dated May 21, 1997.
English Abstract Translation for CN102526455A dated Jul. 4, 2012.
English Abstract Translation for CN101553134A dated Oct. 7, 2009.
English Abstract Translation for CN101514174A dated Aug. 26, 2009.
Anonymous: "Ge132—Abcolyuthiyat ahtiokcidaht", Apr. 21, 2012 (Apr. 21, 2012), XP93090957, Retrieved from the Internet: URL:https://web.archive.org/web/20120421233255/https://antioksidant-ge132.com/ [retrieved on Oct. 12, 2023].
European Patent Application 19189657.0—First communication pursuant to Art. 94(3) EPC dated Nov. 22, 2023.

\* cited by examiner

US 12,064,471 B2

COMPOSITIONS COMPRISING SULFORAPHANE OR A SULFORAPHANE PRECURSOR AND A MUSHROOM EXTRACT OR POWDER

This application is a continuation patent application of U.S. patent application Ser. No. 14/412,191 filed on Dec. 30, 2014, which is the national stage application of International Application No. PCT/US2013/049248 filed on Jul. 3, 2013, the contents of each of which are incorporated herein by reference in their entirety, and also claims priority to the following applications, each of which is incorporated by reference in its entirety: U.S. Provisional Patent Application No. 61/668,328, filed on Jul. 5, 2012; U.S. Provisional Patent Application No. 61/668,342, filed on Jul. 5, 2012; U.S. Provisional Patent Application No. 61/668,386, filed on Jul. 5, 2012; U.S. Provisional Patent Application No. 61/668,396, filed on Jul. 5, 2012; U.S. Provisional Patent Application No. 61/668,364, filed on Jul. 5, 2012; U.S. Provisional Patent Application No. 61/668,374, filed on Jul. 5, 2012; and U.S. Provisional Patent Application No. 61/794,417, filed on Mar. 15, 2013.

FIELD OF THE INVENTION

The present invention relates to the combination of a sulforaphane precursor, an enzyme capable of converting the sulforaphane precursor to sulforaphane, an enzyme potentiator, and a mushroom (preferably maitake, shiitake, or reishi mushroom) extract or powder. The present invention also relates to the combination of sulforaphane or a derivative thereof and a mushroom (preferably maitake, shiitake, or reishi mushroom) extract or powder. The present invention also relates to the combination of a broccoli extract or powder and a mushroom (preferably maitake, shiitake, or reishi mushroom) extract or powder. The present invention provides compositions and methods relating to these combinations.

BACKGROUND OF THE INVENTION

The use of natural products is becoming increasingly popular with humans and companion animals Some of these natural products are being incorporated into dietary supplements and medical foods. There is a need in the art for supplements which are useful as chemoprotective and/or antioxidant agents. In addition, there is a need in the art for pharmaceutical compositions and dietary supplements which are useful for conditions and disorders associated with the breast.

Chemoprotection through the use of natural products is evolving as a safe, effective, inexpensive, easily accessible, and practical means to prevent or reduce the occurrence of many conditions affecting humans and domesticated animals. It is known that carcinogens which can damage cells at the molecular level are often ingested and inhaled as non-toxic precursors. These non-toxic precursors may then convert into carcinogenic substances in the body. Chemoprotective agents, such as natural substances which can activate detoxifying enzymes or their co-factors, can counteract and allow for the elimination or potentiate the other naturally existing defenses such as the immune system.

Some natural products have antioxidant activity. Oxidative stress plays a major role in aging, the progression of neurodegenerative diseases as well as physiological trauma, such as ischemia. Antioxidant agents can reduce or inhibit the oxidation of vital biomolecules and may play a role in treating, preventing, or reducing the occurrence of cancer, coronary heart disease, stroke, and neurodegenerative diseases, Alzheimer's Disease, dementia, and stroke are examples of conditions affected by oxidative stress.

Cancers are largely thought to be a consequence of exposure to environmental challenges—whether from within (i.e. —estrogen, progesterone hormones) or externally (i.e. —bisphenol A (BPA) from plastic)—and chronic inflammation. Fortunately, the damage from environmental challenges can be negated via a complex network of Phase II chemoprotective enzymes found in many cell types of our body. It is well known that estrogens and their metabolites can lead to the proliferation of breast tissue and tumors. Worse, the quinone estrogen metabolites have the capacity to enter the breast tissue and migrate into the nucleus of ductal and glandular epithelial cells. There, they bind to DNA forming quinone estrogen DNA adducts which lead to downstream mutations. These mutations are thought to be responsible for the very foundation of a tumor: cancer initiation. Fortunately, a particular phase II enzyme, NAD(P)H:quinone oxidoreductase (NQO1) can take dangerous and highly reactive quinone estrogens and metabolize them to inert chemicals that can readily be removed from the body. Thus, a major mechanism to decrease cancer incidence is to induce protective Phase II enzymes including NQO1. Increased levels of NQO1 can be effective at treating, preventing, repairing, reducing the occurrence of, decreasing the symptoms associated with any conditions which are resulting from high levels of quinone estrogens. Examples of quinone estrogens include but are not limited to catechol quinones of estrogen. Quinone estrogens are described in the following references, each of which is incorporated by reference in its entirety: Nutter et al. *Chem Res Toxicol*, 1994, 7:23-28; Cavalieri et al. *Ann N Y Acad Sci*, 2006; 1089:286-301; Bolton et al. *Chem Res Toxicol*, 2008, 21(1): 93-101; and Cavalieri et al., *Biochimica et Biophysica Acta*, 2006, 1766:63-78.

An example of a natural product thought to have chemoprotective and antioxidant properties is sulforaphane. Sulforaphane is an organosulfur compound which is also known as 1-isothiocyanato-4-methylsulfinylbutane. The sulforaphane precursor, glucoraphanin, can be obtained from vegetables of the Brassicaceae family, such as broccoli, brussel sprouts, and cabbage. However, copious amounts of vegetables must be consumed in order to obtain levels adequate for chemoprevention. Glucoraphanin is converted into sulforaphane by a thioglucosidase enzyme called myrosinase, which occurs in a variety of exogenous sources such as Brassicaceae vegetables and endogenously in the gut microflora. However, upon ingestion of glucoraphanin, not all animals are capable of achieving its conversion to sulforaphane, most likely due to variations in microflora populations and overall health. In addition, in acidic environments such as the stomach, glucoraphanin can be converted to inert metabolites. The active metabolite, sulforaphane induces nuclear erythroid-2-related factor (Nrf2) which, in turn, upregulates the production of Phase II detoxification enzymes and cytoprotective enzymes such as glutathione S-transferases, NAD(P)H:quinone oxidoreductase (NQO1), and heme-oxygenase-1 (HO-1). Sulforaphane has been thought to induce the production of these enzymes without significantly changing the synthesis of P-450 cytochrome enzymes. The upregulation of Phase II enzymes is thought to play a role in a variety of biological activities, including the protection of the brain from cytotoxicity, the protection of the liver from the toxic effects of fat accumulation, and the detoxification of a variety of other tissues.

Sulforaphane and its precursor glucoraphanin have been studied extensively. Shapiro et al. (*Nutrition and Cancer*, (2006), Vol. 55(1), pp. 53-62) discuss a clinical Phase I study determining the safety, tolerability, and metabolism of broccoli sprout glucosinolates and isothiocyanates. Shapiro et al. discuss a placebo-controlled, double-blind, randomized clinical study of sprout extracts containing either glucosinolates such as glucoraphanin or isothiocyanates such as sulforaphane in healthy human subjects. The study found that administration of these substances did not result in systematic, clinically significant, adverse effects. Ye et al., (*Clinica Chimica Acta*, 200, 316:43-53) discuss the pharmacokinetics of broccoli sprout isothiocyanates in humans.

A number of mushrooms have been used or studied for their medicinal effects. These "medicinal mushrooms" are thought to have beneficial properties, such as antiviral, antimicrobial, anticancer, antihyperglycemic, and/or anti-inflammatory activity. Examples of medicinal mushrooms include maitake, shiitake, reishi, cremini, almond, chestnut, wood ear, cloud ear, porcini, ink cap, yarta gunbu, enokitake, shemeji, tiger milk, morel, bamboo, golden oyster, pink oyster, king oyster, hiratake, cauliflower, white jelly, golden jelly, matsutake, Mexican truffle, and straw mushrooms.

Maitake mushrooms (*Grifola frondosa*) are edible mushroom consumed widely as food and used in traditional medicine to enhance immune function and to treat cancer. Maitake mushrooms, which contain glucans, are thought to have beneficial properties, such as antitumor and immunomodulatory effects. There exist standardized extracts from maitake mushroom that contain as active ingredients glucans such as protein-bound beta-glucans. Beta 1,6-glucan, a protein bound polysaccharide, has been identified as an active constituent in maitake mushrooms. Maitake mushrooms have been demonstrated to have antitumor effects, inhibiting tumor metastasis in vitro. In one study, tumor regression or significant improvements in symptoms were observed in half of the subjects using maitake extract. In a study of postmenopausal breast cancer patients, oral administration of maitake extract was shown to have immunomodulatory effects.

Shiitake mushrooms (*Lentinula edodes*) are edible mushrooms native to East Asia. Shiitake mushrooms contain mycochemicals, which are postulated to have antiviral, antibiotic, anti-inflammatory, antihypertensive and anticarcinogenic effects. This is thought to be largely a result of glucans, both alpha and beta glucans. Some shiitake mushroom extracts have alpha glucan content greater than 40%. Additionally, lentinan (1,3 beta-D-glucan), a polysaccharide isolated from shiitake, has been well studied and is thought to play a role in shiitake's beneficial effects. It has been shown to have anticancer effects in colon cancer cells, which may be due to its ability to suppress cytochrome P450 1A enzymes that are known to metabolize pro-carcinogens to active forms. Lentin, the protein component, has strong antifungal properties and has been found to inhibit proliferation of leukemic cells and suppress the activity of human immunodeficiency virus-1 reverse transcriptase.

Reishi mushrooms (*Ganoderma lucidum*), also known as lingzki mushrooms, are edible mushrooms found in East Asia. Reishi mushrooms are thought to have anti-tumor, anti-cancer, immunomodulatory, and immunotherapeutic effects. Reishi mushrooms have a number of components which are thought to contribute to its activity, including glucan, such as beta-glucan, canthaxanthin, sterols, coumarin, ganoderic acid, and mannitol.

Baker's yeast (*Saccaromyces cerevisiae*) can be a source of glucans, in particular, beta-glucans. The active components of Baker's yeast can be extracted in a number of ways, such as the methods described in Bacon et al. *Biochem J*, 1969, 114(3): 557-567, U.S. Pat. Nos. 7,803,605; 5,702,719; and 8,323,644, each of which is incorporated by reference in its entirety.

Glucans are described in the following references, which are each incorporated by reference in its entirety: Vetvicka et al. *Endocr Metab Immun Disord Drug Targets*, 2009, 9(1):67-75, and Vetvicka et al. *J Med Food*, 2008: 11(4): 615-622.

Zhang et al. (*Proc. Natl. Acad. Sci.*, (1994), Vol. 91, pp. 3147-3150) discusses a study in Sprague-Dawley rats to determine the anticarcinogenic activities of sulforaphane and structurally related synthetic norbornyl isiothiocyanates. The study determined that administration of sulforaphane was effective in blocking the formation of mammary tumors.

Cornblatt et al. (*Carcinogenesis*, (2007), Vol. 38(7): pp. 1485-1490) discusses a study in Sprague-Dawley rats to determine the effect of sulforaphane in chemoprevention in the breast. The study determined that oral administration of either sulforaphane resulted in a 3-fold increase in NAD(P)H:quinone oxidoreductase (NQO1) enzymatic activity and a 4-fold elevated immunostaining of the heme oxygenase-1 (HO-1) enzyme in the mammary epithelium.

Munday et al. (*Cancer Res*, (2008), Vol. 68(5): pp. 1593-1600) discusses a study regarding the effects of a freeze-dried aqueous extract of broccoli sprouts on bladder cancer development in rats. The study found that administration of the broccoli sprout extract resulted in a significant induction of glutathione S-transferase and NAD(P)H:quinone oxidoreductase 1 in the bladder, which are enzymes having protective activity against oxidants and carcinogens.

Fang et al. (*J Altern Complem Med*, (2006), Vol. 12(2): pp. 125-132) discloses a study determining the antiproliferative effect of an ethyl acetate fraction of shiitake mushrooms on human breast carcinoma cell lines (MDA-MB-453 and MCF-7), a human nonmalignant breast epithelial cell line (MCF-10F), and two myeloma cell lines (RPMI08226 and IM-9). The study found that the inhibition of growth of tumor cells by the components in shiitake mushrooms may result from the induction of apoptosis.

Kim et al. (*J Med Food*, (2007), Vol. 10(1): pp. 25-31) discloses a study investigating the activation of natural killer (NK) cells and anticancer effects of an exo-biopolymer from rice bran cultured from *Lentinus edodes*. The study found that the exo-biopolymer may be effective for preventing and/or treating cancer through natural killer cell activation.

Louie et al. (*BJUI*, (2009), Vol. 153(9): pp. 1215-1221) discusses the synergistic effect of the combination of interferon-α and maitake mushroom D-fraction (PDF), a bioactive mushroom extract on anticancer activity of interferon-α in bladder cancer T24 cells in vitro.

Masuda et al. (*Biol. Pharm. Bull.* (2008), Vol. 31(6): pp. 1104-1108) discusses a study assessing the anti-metastatic activity of a fraction of maitake mushrooms in a murine model of lung metastasis. The study found that the fraction inhibited tumor metastasis by activation of natural killer cells and antigen-presenting cells (APCs) and suppressing adhesion molecules such as ICAM-1, leading to the inhibition of tumor cell adhesion to vascular endothelial cells.

European Patent Application No. 2 213 280 discloses formulations comprising glucosinolates such as glucoraphanin, and myrosinase, wherein the formulation is encapsulated or coated.

All references cited herein are incorporated by reference in their entirety.

SUMMARY OF THE INVENTION

The present invention provides a composition comprising: (i) a sulforaphane precursor, preferably glucoraphanin; (ii) an enzyme capable of converting the sulforaphane precursor to sulforaphane, preferably a glucosidase enzyme, more preferably a thioglucosidase enzyme, and most preferably myrosinase; (iii) an enzyme potentiator or cofactor, preferably ascorbic acid; and (iv) a mushroom (preferably maitake, shiitake, or reishi mushroom) extract or powder. The present invention also provides a method of treating, preventing, reducing the occurrence of, decreasing the symptoms associated with, and/or reducing secondary recurrences of, cancer, in particular breast cancer, prostate cancer, colon cancer, lung cancer, and bladder cancer in a subject, comprising administering to the subject: (i) a sulforaphane precursor, (ii) an enzyme capable of converting the sulforaphane precursor to sulforaphane, (iii) an enzyme potentiator, and (iv) a mushroom (preferably maitake, shiitake, or reishi mushroom) extract or powder. The present invention also provides a method of increasing levels or increasing gene expression of NAD(P)H:quinone oxidoreductase 1 (NQO-1) in a subject, comprising administering to the subject: (i) a sulforaphane precursor, (ii) an enzyme capable of converting the sulforaphane precursor to sulforaphane, (iii) an enzyme potentiator, and (iv) a mushroom (preferably maitake, shiitake, or reishi mushroom) extract or powder. The present invention also provides a method of treating, preventing, reducing the occurrence of, decreasing the symptoms associated with, and/or reducing secondary recurrences of a disease or condition associated with elevated levels of quinone estrogen, comprising administering to the subject: (i) a sulforaphane precursor, (ii) an enzyme capable of converting the sulforaphane precursor to sulforaphane, (iii) an enzyme potentiator, and (iv) a mushroom (preferably maitake, shiitake, or reishi mushroom) extract or powder.

The present invention provides a composition comprising: (i) sulforaphane or a derivative thereof, and (ii) a mushroom (preferably maitake, shiitake, or reishi mushroom) extract or powder. The present invention also provides a method of treating, preventing, reducing the occurrence of, decreasing the symptoms associated with, and/or reducing secondary recurrences of, cancer, in particular breast cancer, prostate cancer, colon cancer, lung cancer, and bladder cancer in a subject, comprising administering to the subject: (i) sulforaphane or a derivative thereof, and (ii) a mushroom (preferably maitake, shiitake, or reishi mushroom) extract or powder. The present invention also provides a method of increasing levels or increasing gene expression of NAD(P)H:quinone oxidoreductase 1 (NQO-1) in a subject, comprising administering to the subject, comprising administering to the subject: (i) sulforaphane or a derivative thereof, and (ii) a mushroom (preferably maitake, shiitake, or reishi mushroom) extract or powder. The present invention also provides a method of treating, preventing, reducing the occurrence of, decreasing the symptoms associated with, and/or reducing secondary recurrences of a disease or condition associated with elevated levels of quinone estrogen, comprising administering to the subject: (i) sulforaphane or a derivative thereof, and (ii) a mushroom (preferably maitake, shiitake, or reishi mushroom) extract or powder.

The present invention provides a composition comprising: (i) a broccoli extract or powder, and (ii) a mushroom (preferably maitake, shiitake, or reishi mushroom) extract or powder. The present invention also provides a method of treating, preventing, reducing the occurrence of, decreasing the symptoms associated with, and/or reducing secondary recurrences of, cancer, in particular breast cancer, prostate cancer, colon cancer, lung cancer, and bladder cancer in a subject, comprising administering to the subject: (i) a broccoli extract or powder, and (ii) a mushroom (preferably maitake, shiitake, or reishi mushroom) extract or powder. The present invention also provides a method of increasing levels or increasing gene expression of NAD(P)H:quinone oxidoreductase 1 (NQO-1) in a subject, comprising administering to the subject, comprising administering to the subject: (i) a broccoli extract or powder, and (ii) a mushroom (preferably maitake, shiitake, or reishi mushroom) extract or powder. The present invention also provides a method of treating, preventing, reducing the occurrence of, decreasing the symptoms associated with, and/or reducing secondary recurrences of a disease or condition associated with elevated levels of quinone estrogen, comprising administering to the subject: (i) a broccoli extract or powder, and (ii) a mushroom (preferably maitake, shiitake, or reishi mushroom) extract or powder.

DETAILED DESCRIPTION OF THE INVENTION

Figure 1:
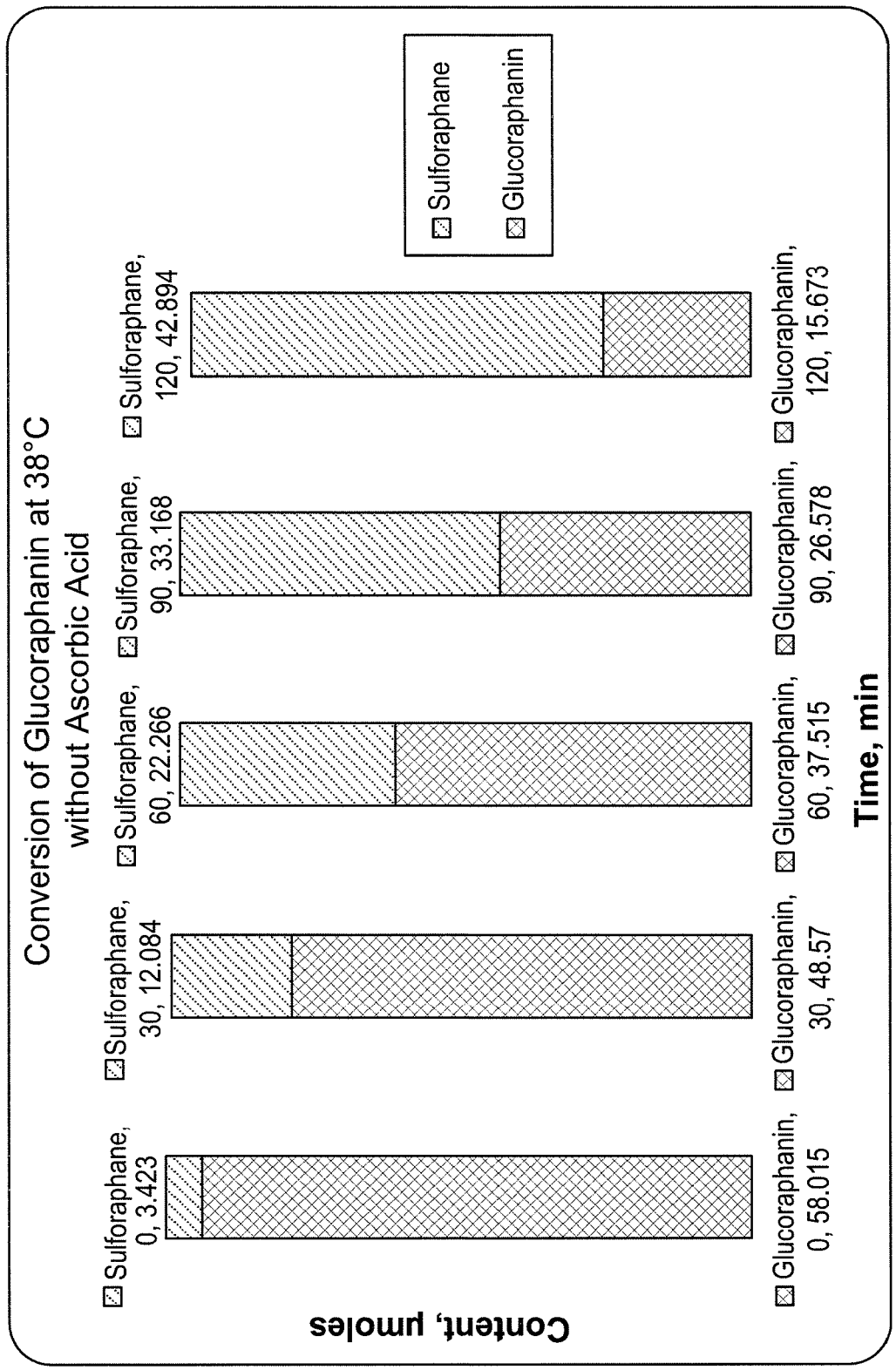
FIG. 1 is a graph showing the conversion of glucoraphanin at 38° C. without ascorbic acid, as described in Example 4.
Figure 2:
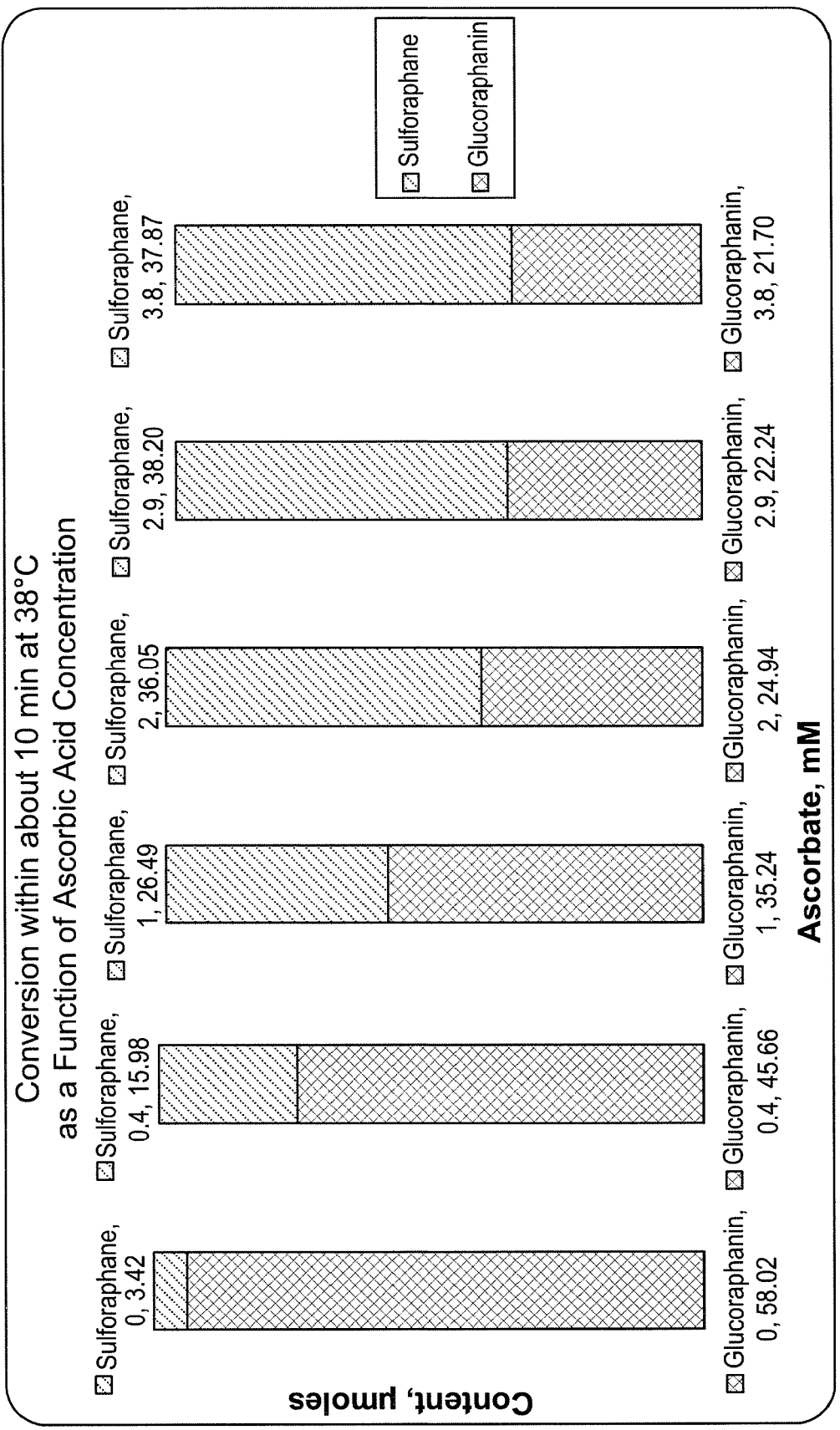
FIG. 2 is a graph showing the conversion within about 10 minutes at 38° C. as a function of ascorbic acid concentration, as described in Example 4.
Figure 3:
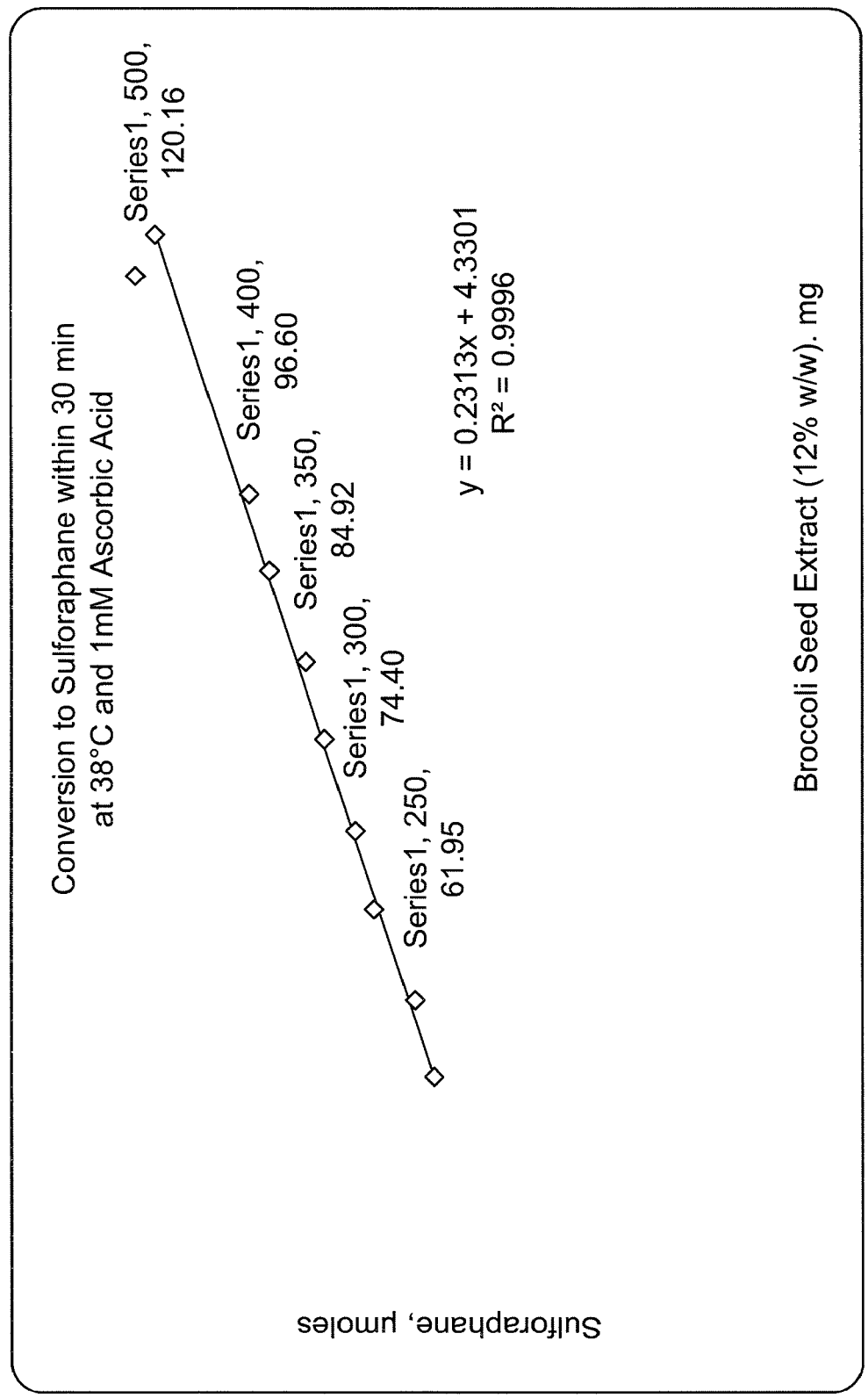
FIG. 3 is a graph showing the conversion to sulforaphane within 30 minutes at 38° C. and 1 mM ascorbic acid, as described in Example 4.

The present invention relates to the combination of a sulforaphane precursor, an enzyme capable of converting the sulforaphane precursor to sulforaphane, an enzyme potentiator, and a mushroom (such as maitake, shiitake, or reishi mushroom) extract or powder. The present invention also relates to the combination of sulforaphane or a derivative thereof and a mushroom (such as maitake, shiitake or reishi mushroom extract or powder. The present invention also relates to the combination of a broccoli extract or powder and a maitake, shiitake, or reishi mushroom extract or powder. The present invention also relates to the use of a mushroom extract or powder, with a mixture of one or more of the following: sulforaphane precursor, sulforaphane or a derivative thereof, and broccoli extract. The present invention provides compositions relating to these combinations.

The present invention also provides methods comprising administering these combinations. In some embodiments, the combination may be administered for treating, preventing, reducing the occurrence of, decreasing the symptoms associated with, and/or reducing secondary recurrences of, cancer, in particular breast cancer, prostate cancer, colon cancer, lung cancer, and bladder cancer in a subject, comprising administering to the subject. In some embodiments, the combination may be administered for increasing levels or increasing gene expression of NAD(P)H:quinone oxidoreductase 1 (NQO-1) in a subject. In some embodiments, the combination may be administered for treating, preventing, reducing the occurrence of, decreasing the symptoms associated with, and/or reducing secondary recurrences of a disease or condition associated with elevated levels of quinone estrogen.

Sulforaphane is also known as 1-isothiocyanato-4-methylsulfinylbutane. Derivatives of sulforaphane include, but are not limited to sulfoxythiocarbamate analogues of sulforaphane, 6-methylsulfinylhexyl isothiocyanate (6-HITC), and compounds which comprise the structure of sulforaphane with different side chains and/or various lengths of spacers between the isothiocyanato and sulfoxide groups. Examples of derivatives of sulforaphane include those described in the following references, each of which is incorporated herein by reference: Hu et al., *Eur J Med Chem*, 2013, 64:529-539; Ahn et al., *Proc Natl Acad Sci USA*, 2010, 107(21):9590-9595; and Morimistu et al., *J. Biol. Chem.* 2002, 277:3456-3463, and Baird et al., *Arch Toxicol*, 2011, 85(4):241-272.

In some embodiments, the composition comprises sulforaphane or a derivative thereof, preferably sulforaphane, in an amount of about 1 μg to about 10 g, preferably about 3 μg to about 5 g, preferably about 5 μg to about 1000 mg, preferably about 7 μg to about 750 mg, more preferably about 10 μg to about 500 mg, and most preferably about 100 μg to about 100 mg. In some embodiments, compositions suitable for human use comprise about 1 mg to about 20 mg.

In some embodiments, the methods of the present invention comprise administration of sulforaphane or a derivative thereof to a subject, preferably sulforaphane, in an amount of about 1 μg to about 10 g, preferably about 3 μg to about 5 g, preferably about 5 μg to about 1000 mg, preferably about 7 μg to about 750 mg, more preferably about 10 μg to about 500 mg, and most preferably about 100 μg to about 100 mg. In some embodiments wherein the subject is human, the method comprises administration of about 1 mg to about 20 mg. In some embodiments, the methods of the present invention comprise administration of sulforaphane or a derivative thereof to a subject, preferably sulforaphane, in an amount of about 0.01 μg/kg to about 0.2 g/kg, preferably about 0.05 μg/kg to about 0.07 g/kg, more preferably about 0.07 μg/kg to about 15 mg/kg, more preferably about 0.1 μg/kg to about 11 mg/kg, and most preferably about 0.2 μg/kg to about 7 mg/kg. In some embodiments wherein the subject is human, the method comprises administration of about 2 μg/kg to about 2 mg/kg, and more preferably about 0.01 mg/kg to about 0.3 mg/kg. The above amounts may refer to each dosage administration or a total daily dosage. The total daily dosage refers to the total amount of a compound or ingredient which is administered to a subject in a twenty-four hour period.

In some embodiments, the method comprises administration of more than one of a sulforaphane or a derivative thereof. In some embodiments, the compositions comprise more than one of a sulforaphane or a derivative thereof. For example, the methods or composition may comprise both sulforaphane and one or more derivatives thereof, or two or more derivatives. In some embodiments wherein the method or composition comprise more than one of a sulforaphane or a derivative thereof, the above amounts may refer to the amount of each sulforaphane or a derivative thereof, or the total amount of the more than one sulforaphane or derivative thereof.

The term "sulforaphane precursor" refers to any compound, substance or material which can be used to produce sulforaphane. In preferred embodiments, the sulforaphane precursor comprises a compound which can be converted or metabolized to sulforaphane, preferably by an enzyme. In some preferred embodiments, the sulforaphane precursor comprises glucoraphanin. Glucoraphanin is a glucosinolate which is also known as 4-methylsulfinylbutyl glucosinolate and 1-S-[(1E)-5-(methylsulfinyl)-N-(sulfonatooxy) pentanimidoyl]-1-thio-β-D-glucopyranose.

In some embodiments, the composition comprises about 1 μg to about 10 g, preferably about 250 μg to about 5 g, more preferably about 500 μg to about 2000 mg, even more preferably about 1 mg to about 750 mg, even more preferably about 1.5 mg to about 250 mg, even more preferably about 2 mg to about 100 mg, and most preferably about 3 mg to about 75 mg of the sulforaphane precursor, preferably glucoraphanin. In some embodiments, compositions suitable for human use comprise about 3.5 mg to about 50 mg of the sulforaphane precursor, preferably glucoraphanin.

In some embodiments, the method comprises administering the sulforaphane precursor, preferably glucoraphanin to a subject, in an amount of about 1 μg to about 10 g, preferably about 250 μg to about 5 g, more preferably about 500 μg to about 2000 mg, even more preferably about 1 mg to about 750 mg, even more preferably about 1.5 mg to about 250 mg, even more preferably about 2 mg to about 100 mg, and most preferably about 3 mg to about 75 mg. In some embodiments wherein the subject is a human, the method comprises administration of about 3.5 mg to about 50 mg. In some embodiments, the method comprises administering an amount of sulforaphane precursor to a subject in an amount of about 1 μg/kg to about 1000 mg/kg, preferably about 5 μg/kg to about 500 mg/kg, more preferably about 7.5 μg/kg to about 100 mg/kg, even more preferably about 10 μg/kg to about 25 mg/kg, and most preferably about 25 μg/kg to about 10 mg/kg. In some embodiments wherein the subject is a human, the method comprises administration of about 50 μg/kg to about 800 μg/kg. The above amounts may refer to each dosage administration or a total daily dosage.

In some embodiments, the method comprises administration of more than one sulforaphane precursor. In some embodiments, the composition comprises more than sulforaphane precursor. In some embodiments wherein the method or composition comprises more than one sulforaphane precursor, the above amounts may refer to the amount of each sulforaphane precursor, or the total amount of the sulforaphane precursors.

The sulforaphane precursor may be converted or metabolized to sulforaphane. In some embodiments, the sulforaphane precursor is converted to sulforaphane by an enzyme. In some embodiments, the enzyme capable of converting the sulforaphane precursor to sulforaphane comprises a glucosidase enzyme, preferably a thioglucosidase enzyme, and more preferably myrosinase. Myrosinase is also known as thioglucoside glucohydrolase.

In some embodiments, the composition comprises the enzyme in an amount of about 1 pg to about 1 μg, preferably about 50 pg to about 500 ng, and most preferably about 1 ng to about 150 ng. In some embodiments, compositions suitable for human use comprise about 5 ng to about 75 ng of the enzyme.

In some embodiments, the method comprises administering the enzyme, preferably myrosinase, in an amount of about 1 pg to about 1 µg, preferably about 50 pg to about 500 ng, and most preferably about 1 ng to about 150 ng. In some embodiments wherein the subject is a human, the method comprises administration of about 5 ng to about 75 ng of the enzyme. In some embodiments, the method comprises administering the enzyme to a subject in an amount of about 0.02 pg/kg to about 0.02 ug/kg, preferably about 0.7 pg/kg to about 7 ng/kg, and most preferably about 0.02 ng/kg to about 2 ng/kg. In some preferred embodiments wherein the subject is a human, the method comprises administration of about 0.1 ng/kg to about 1 ng/kg. The above amounts may refer to each dosage administration or a total daily dosage.

In some embodiments, the method comprises administration of more than one enzyme capable of converting the sulforaphane precursor to sulforaphane. In some embodiments, the composition comprises more than one enzyme capable of converting the sulforaphane precursor to sulforaphane. In some embodiments wherein the methods or compositions comprise more than one enzyme, the above amounts may refer to the amount of each enzyme, or the total amount of the enzymes.

The present invention also provides for the use of a broccoli extract and/or powder, including but not limited to broccoli seed and sprout extracts and powders. The present invention provides methods of administration of broccoli extract and/or powder, and compositions comprising broccoli extract and/or powder. In some embodiments, the broccoli extract or powder is standardized to contain about 1% to about 75% w/w, more preferably about 2.5% to about 50%, even more preferably about 5% to about 25%, and most preferably about 10% to about 20% of a sulforaphane precursor, preferably glucoraphanin. Examples of broccoli extracts and powders include but are not limited to those described in U.S. Pat. Nos. 5,411,986; 5,725,895; 5,968,505; 5,968,567; 6,177,122; 6,242,018; 6,521,818; 7,303,770; and 8,124,135, each of which is incorporated by reference in its entirety. Powders of broccoli may be obtained, for example, by air drying, freeze drying, drum drying, spray drying, heat drying and/or partial vacuum drying broccoli, preferably broccoli sprouts. In some embodiments, the compositions and methods comprise use of about 1 µg to about 10 g, more preferably about 250 µg to about 5 g, even more preferably about 500 µg to about 1 g, preferably about 600 µg to about 500 mg, more preferably about 750 µg to about 400 mg, and most preferably about 1 mg to about 300 mg of the broccoli extract. In some embodiments, the broccoli extract or powder is present in a composition or administered to a subject in amounts sufficient to provide a sulforaphane precursor or sulforaphane in the amounts described above. In some embodiments, the composition may further comprise an enzyme potentiator, preferably ascorbic acid. In some embodiments, the method may further comprise administration of an enzyme potentiator, preferably ascorbic acid.

The sulforaphane or a derivative thereof, the sulforaphane precursor, and/or the enzyme capable of converting the sulforaphane precursor to sulforaphane may be obtained from any source, including but not limited to one or more plants from the Brassicaceae (also known as Cruciferae) family Examples of plants from the Brassicaceae family include, but are not limited to, the following: broccoli, Brussels sprouts, cauliflower, cabbage, horseradish, parsnip, radish, wasabi, watercress, and white mustard. In some preferred embodiments, sulforaphane precursor, preferably glucoraphanin, and the enzyme, preferably myrosinase, are obtained from broccoli, broccoli sprouts, or broccoli seeds. The sulforaphane precursor and the enzyme may be obtained from the same source or from different sources. In some embodiments, both the sulforaphane precursor and the enzyme may be obtained from an extract or powder from these plants, preferably a broccoli seed or sprout extract or powder.

The present invention provides for the use of an enzyme potentiator or cofactor. Enzyme potentiators may be used to enhance the activity of the enzyme that is capable of converting the sulforaphane precursor to sulforaphane. In some embodiments, the enzyme potentiator comprises an enzyme co-factor, preferably ascorbic acid. Ascorbic acid, also known as ascorbate or vitamin C, can potentiate the activity of myrosinase. In some embodiments, without an enzyme potentiator such as ascorbic acid, the conversion reaction to sulforaphane may be too slow to occur in the location needed for peak absorption. The enzyme potentiator may be obtained from a natural source, or it may be produced synthetically.

In some embodiments, the compositions may comprise about 1 mg to about 500 mg, preferably about 1 mg to about 250 mg, and most preferably about 1 mg to about 125 mg of the enzyme potentiator. In some embodiments, compositions suitable for human use comprise about 1 mg to about 50 mg of the enzyme potentiator.

In some embodiments, the method of the present invention comprises administration of an enzyme potentiator, preferably ascorbic acid, in an amount of about 1 mg to about 500 mg, preferably 1 mg to about 250 mg, and most preferably about 1 mg to about 125 mg. In some embodiments wherein the subject is a human, the method comprises administration of about 1 mg to about 50 mg. In some embodiments, the method of the present invention comprises administration of the enzyme potentiator, preferably ascorbic acid, in an amount of about 0.01 mg/kg to about 3 mg/kg, and most about 0.02 mg/kg to about 2 mg/kg. In some embodiments wherein the subject is a human, the method comprises administration of about 0.02 mg/kg to about 0.7 mg/kg of the enzyme potentiator. The above amounts may refer to each dosage administration or a total daily dosage.

In some embodiments, the method comprises administration of more than one enzyme potentiator. In some embodiments, the composition comprises more than one an enzyme potentiator. In some embodiments wherein the method or composition comprises more than one enzyme potentiator, the above amounts may refer to the amount of each enzyme potentiator, or the total amount of the enzyme potentiators.

The present invention provides for the use of a mushroom extract or powder. In some embodiments, the mushrooms may comprise "medicinal mushrooms," including, but not limited to maitake, shiitake, reishi, cremini, almond, chestnut, wood ear, cloud ear, porcini, ink cap, yarta gunbu, enokitake, shemeji, tiger milk, morel, bamboo, golden oyster, pink oyster, king oyster, hiratake, cauliflower, white jelly, golden jelly, matsutake, Mexican truffle, and straw mushrooms. In preferred embodiments, the mushroom comprises maitake mushroom, shiitake mushroom, reishi mushroom, and/or a mixture of one or more of these.

Maitake mushroom belongs to the species *Grifola frondosa*. Maitake mushroom may contain a number of fractions having biological activity. Examples of components found in maitake mushroom include but are not limited to: glucans (such as alpha-glucans and beta-glucans); lipids (such as octadecanoic and octadecadienoic acids); phospholipids (such as phosphatidylethanolamine, phosphatidylcholine, phosphatidylinositol, phosphatidylserine and phosphatidic acid).

Shiitake mushroom belongs to the species *Lentinula edodes*. Shiitake mushroom may contain a number of fractions having biological activity. Examples of components found in shiitake mushrooms include but are not limited to: glucans (such as alpha-glucans and beta-glucans), proteins (such as lentin); lipids (such as linoleic acid); and lignins.

Reishi mushrooms belong to the species *Ganoderma lucidum*. Reishi mushrooms may contain a number of fractions having biological activity. Examples of components found in reishi mushroom include but are not limited to: glucan (such as alpha-glucans and beta-glucans), canthaxanthin, sterols, coumarin, ganoderic acid, and mannitol.

In some preferred embodiments, the mushroom extract or powder comprises one or more glucans. A glucan is a polysaccharide of a D-glucose monomer linked by glycosidic bonds and may be in the alpha or beta form. In some embodiments, the glucan comprises one or more alpha-glucan and/or beta-glucans. Alpha-glucans include, but are not limited to, 1,4-α-glucans and 1,6-α-glucans and beta-glucans include, but are not limited to, 1,3-β-glucans, 1,4-β-glucans, and 1,6-β-glucans. The glucans may be expressed in a variety of polymeric configurations. In preferred embodiments, the maitake mushroom extract or powder comprises 1,3-β-glucans and/or 1,6-β-glucans. In preferred embodiments, the shiitake mushroom extract or powder comprises 1,4-α-glucans. In preferred embodiments, the reishi mushroom extract or powder comprises 1,3-β-glucans and/or 1,6-β-glucans. In some embodiments, the compositions and methods of the present invention may comprise use of glucans in a purified form or glucans produced synthetically, instead of a mushroom extract or powder.

In some embodiments, a maitake mushroom extract or powder may be used. In some embodiments, the maitake mushroom extract or powder is standardized to contain about 1% to about 75%, more preferably about 5% to about 50%, even more preferably about 10% to about 30%, and most preferably about 15% to about 20% of one or more glucans, preferably beta-glucans, and more preferably 1,3-beta glucan and/or 1,6-beta-glucan. Examples of maitake mushroom extracts and powders include, but are not limited to, those described in U.S. Pat. No. 5,854,404; WO 2007142130; EP 0893449; WO2009063885; WO2006107208; WO2007024496; and WO2001054673, each of which is incorporated by reference in its entirety. Powders of maitake mushroom may be obtained, for example, by air drying, freeze drying, drum drying, spray drying, heat drying and/or partial vacuum drying maitake mushrooms. In some embodiments, the composition comprises about 250 µg to about 100 mg, preferably about 500 µg to about 75 mg, and most preferably about 750 µg to about 50 mg. In some embodiments, compositions suitable for humans comprise about 1 mg to about 20 mg of maitake mushroom extract. In some embodiments, the method comprises administration of about 250 µg to about 100 mg, preferably about 500 µg to about 75 mg, and most preferably about 750 µg to about 50 mg. In some embodiments wherein the subject is human, the method comprises administration of about 1 mg to about 20 mg of maitake mushroom extract. The above amounts may refer to each dosage administration or a total daily dosage.

In some embodiments, a shiitake mushroom extract or powder may be used. In some embodiments, the shiitake mushroom extract or powder is standardized to contain about 1% to about 75%, preferably about 10% to about 60%, even more preferably about 25% to about 50%, and most preferably about 30% to about 40% of one or more glucans, preferably alpha-glucans, and more preferably 1,4-alpha-glucan. Examples of shiitake mushroom extracts include, but are not limited to, those described in U.S. Pat. Nos. 5,780,097; 6,582,723; WO2005107496, WO2007024496, and WO2000033069, each of which is incorporated by reference in its entirety. Powders of shiitake mushroom may be obtained, for example, by air drying, freeze drying, drum drying, spray drying, heat drying and/or partial vacuum drying maitake mushrooms. In some embodiments, the composition comprises about 1 mg to about 1 g, preferably about 10 mg to about 500 mg, and most preferably about 25 mg to about 300 mg. In some embodiments, compositions suitable for humans comprise about 50 mg to about 250 mg of shiitake mushroom extract or powder. In some embodiments, the method comprises administration of about 1 mg to about 1 g, preferably about 10 mg to about 500 mg, and most preferably about 25 mg to about 300 mg. In some preferred embodiments wherein the subject is human, the method comprises administration of about 50 mg to about 250 mg of shiitake mushroom extract or powder to a subject. The above amounts may refer to each dosage administration or a total daily dosage. The above amounts may refer to each dosage administration or a total daily dosage.

In some embodiments, a reishi mushroom extract or powder may be used. In some embodiments, the reishi mushroom extract comprises about 1% to about 75%, more preferably about 5% to about 50%, even more preferably about 10% to about 30%, and most preferably about 15% to about 20% of one or more glucans, preferably beta-glucans, and more preferably 1,3-beta glucan and/or 1,6-beta-glucan. Powders of reishi mushroom may be obtained, for example, by air drying, freeze drying, drum drying, spray drying, heat drying and/or partial vacuum drying maitake mushrooms.

In some embodiments, the composition and/or method comprises use of one type or mushroom extract or powder, such as maitake mushroom extract or powder, shiitake mushroom extract or powder or reishi mushroom extract or powder. In some embodiments, the composition and/or method comprises use of a mixture of one or more types of mushroom extract or powder. In some embodiments, the composition and/or method comprises use of a mixture of one or more of the following: maitake mushroom extract or powder, shiitake mushroom extract or powder, and reishi mushroom extract or powder. The composition and method may comprise use of an extract or a powder, or a mixture of extracts and powders.

The present invention also provides for the use of any glucan-rich component in place of, or in addition to, the mushroom extract or powder. An example of a glucan-rich component is Baker's yeast. In some embodiments, yeast preparations may be used. In some embodiments, the yeast preparation comprises about 0.1% to about 50%, preferably about 0.5% to about 25%, and most preferably about 0.5% to about 10% of one or more glucans. Examples of yeast preparations include those discussed in U.S. Pat. Nos. 5,223,491 and 5,576,015, each of which is incorporated by reference in its entirety.

The methods of the present invention may further comprise administration of one or more additional components. The compositions of the present invention may further comprise one or more additional components. The additional components may include active pharmaceutical ingredients, nutritional supplements, and nutritional extracts. Examples of additional components include, but are not limited, ursolic acid, quercetin or a derivative thereof, an aminosugar such as glucosamine, a glycosaminoglycan such as chondroitin, avocado/soybean unsaponifiables, vitamins such as vitamin K2, coffee fruit, magnesium, ursolic acid, proanthocyanidins, alpha- and beta-glucans, curcumin, phytosterols, phytostanols, and S-adenosylmethionine (SAMe). These additional components may be present in milk thistle (*Silybum marianum*) extract (silymarin), cranberry (*Vaccinium macrocarpon*) extract (proanthocyanidins, quercetin, and ursolic acid), turmeric (*Curcuma longa*).

In some embodiments, the ratio of beta-glucan to sulforaphane or a derivative of (beta-glucan:sulforaphane or a derivative of) is about 50:1 to about 1:50, preferably about 25:1 to about 1:25, more preferably about 10:1 to about 1:20, more preferably about 5:1 to about 1:10, even more preferably about 1:1 to about 1:8, and most preferably about 1:3 to about 1:5. In some embodiments, the ratio of alpha-glucan to sulforaphane or a derivative of (alpha-glucan:sulforaphane or a derivative of) is about 1:50 to about 50:1, preferably about 1:10 to about 25:1, more preferably about 1:5 to about 20:1, more preferably about 1:1 to about 15:1, even more preferably about 2:1 to about 10:1, and most preferably about 3:1 to about 8:1. In some embodiments, the ratio of beta-glucan to sulforaphane precursor of (beta-glucan:sulforaphane precursor) is about 50:1 to about 1:50, preferably about 30:1 to about 1:35, more preferably about 20:1 to about 1:25, more preferably about 10:1 to about 1:20, even more preferably about 5:1 to about 1:15, and most preferably about 1:1 to about 1:10. In some embodiments, the ratio of alpha-glucan to precursor (alpha-glucan:precursor) is about 1:50 to about 100:1, preferably about 1:25 to about 75:1, more preferably about 1:10 to about 50:1, more preferably about 1:5 to about 40:1, even more preferably about 1:1 to about 30:1, and most preferably about 2:1 to about 20:1

In some embodiments, the composition comprises a unit dosage form, including but not limited to pharmaceutical dosage forms suitable for oral, rectal, intravenous, subcutaneous, intramuscular, transdermal, transmucosal, and topical. In some preferred embodiments, the composition comprises an orally administrable dosage form or a rectally administrable dosage form. Examples of orally administrable dosage forms include, but are not limited to a tablet, capsule, powder that can be dispersed in a beverage, a liquid such as a solution, suspension, or emulsion, a soft gel/chew capsule, a chewable bar, or other convenient dosage form known in the art. In preferred embodiments, the composition comprises a tablet, capsule, or soft chewable treat. The orally administrable dosage forms may be formulated for immediate release, extended release or delayed release.

In some embodiments, at least the sulforaphane precursor, the enzyme, and the enzyme potentiator are provided in a dosage form which allows for the release in an area of the gastrointestinal tract having a pH of at least 4 and preferably at least 5, such as the small intestine, preferably the duodenum. In some embodiments, at least the sulforaphane or derivative thereof and/or the broccoli extract or powder are provided in a dosage form which allows for the release in an area of the gastrointestinal tract having a pH of at least 4 and preferably at least 5, such as the small intestine, preferably the duodenum. In some embodiments, the mushroom extract or powder and/or any optional additional components are also released in an area of the gastrointestinal tract having a pH of at least 4 and preferably at least 5, such as the small intestine, preferably the duodenum. The small intestine includes the duodenum, jejunum, and ileum.

In some embodiments, each of these components (i.e, sulforaphane precursor, enzyme, enzyme potentiator, sulforaphane or a derivative thereof, broccoli extract or powder, mushroom extract or powder, and/or additional components) are released simultaneously or concomitantly (i.e., within a short period of time of each other). This provides benefits over glucoraphanin-containing compositions formulated to release the glucoraphanin in an area of the gastrointestinal tract having a pH below 4, such as the stomach. In low pH environments such as this, the acidic environment may divert conversion of sulforaphane precursor to other, physiologically inactive end products, such as sulforaphane nitrile and epithionitrile.

In some embodiments, the compositions may comprise orally administrable compositions which comprise enteric coated dosage forms or any dosage form which is resistant to degradation in an area of the gastrointestinal tract having pH below 4, such as the stomach. For example, the orally administrable composition may comprise a tablet or capsule comprising an enteric coating. The enteric coating may comprise materials including, but not limited to cellulose acetate phthalate, hydroxypropyl methylcellulose phthalate, polyvinyl acetate phthalate, methacrylic acid copolymer, methacrylic acid: acrylic ester copolymer, hydroxypropyl methylcellulose acetate succinate, hydroxypropyl methylcellulose trimellitate, shellac, cellulose acetate trimellitate, carboxymethylethylcellulose, and mixtures thereof. The enteric coating may comprise any suitable enteric polymers known in the art. In some embodiments, one or more of the components in the composition may be embedded in a matrix of enteric polymers. In some embodiments, the orally administrable compositions comprise a capsule that dissolves slowly in gastric acid and travels to the small intestine, such as DRCAPS™ acid resistant capsules, which are marketed by CAPSUGEL® or any other acid resistant capsules.

In the most preferred form, the orally administrable composition is surrounded by a coating that does not dissolve unless the surrounding medium is at a pH of at least 4, and more preferably at least 5. Alternatively, a coating may be employed which controls the release by time, as opposed to pH, with the rate adjusted so that the components are not released until after the pH of the gastrointestinal tract has risen to at least 4, and more preferably at least 5. Thus, a time-release formulation may be used to prevent gastric presence of the sulforaphane precursor, the enzyme capable of converting the sulforaphane precursor to sulforaphane, and the enzyme potentiator, or of the sulforaphane. The coating layer(s) may be applied onto orally administrable composition using standard coating techniques. The enteric coating materials may be dissolved or dispersed in organic or aqueous solvents. The pH at which the enteric coat will dissolve can be controlled by a polymer, or combination of polymers, selected and/or ratio of pendant groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates or other plasticizers. Additives such as dispersants, colorants, antiadhering and anti-foaming agents may also be included.

The compositions may contain one or more non-active pharmaceutical ingredients (also known generally as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. The excipients are preferably pharmaceutically acceptable excipients. Examples of classes of pharmaceutically acceptable excipients include lubricants, buffering agents, stabilizers, blowing agents, pigments, coloring agents, flavoring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof.

In some embodiments, the combination of (i) a sulforaphane precursor, preferably glucoraphanin, (ii) an enzyme capable of converting the sulforaphane precursor to sulforaphane, preferably a glucosidase enzyme, more preferably a thioglucosidase enzyme, and most preferably myrosinase, (iii) an enzyme potentiator, preferably an enzyme co-factor, more preferably ascorbic acid, and (iv) a mushroom extract or powder (which contains glucans) demonstrates a synergistic effect. In some embodiments, the combination of sulforaphane (or a derivative thereof) and a mushroom extract or powder (which contains glucans) demonstrates a synergistic effect. Synergy refers to the effect wherein a combination of two or more components provides a result which is greater than the sum of the effects produced by the agents when used alone. In preferred embodiments, the synergistic effect is greater than an additive effect. In some embodiments, the combination of a sulforaphane precursor, an enzyme capable of converting the sulforaphane precursor to sulforaphane, an enzyme potentiator, and a maitake, shiitake, or reishi mushroom extract or powder has a statistically significant, greater effect compared to: (i) each component alone, (ii) the combination of sulforaphane precursor and the enzyme alone; and/or (iii) the combination of sulforaphane precursor, the enzyme, and the enzyme potentiator alone.

In preferred embodiments, the combination of the sulforaphane precursor, the enzyme, the enzyme potentiator, and a mushroom extract or powder (which contains glucans) demonstrates synergy by having a statistically significant and/or greater than additive effect compared to the sulforaphane precursor alone and the mushroom extract or powder alone. In some embodiments, the combination of glucoraphanin, myrosinase, ascorbic acid, and a mushroom extract or powder has a synergistic effect compared to the combination of glucoraphanin, myrosinase, ascorbic acid alone; and compared to glucans alone.

In some embodiments, the combination of a sulforaphane (or a derivative thereof) and a mushroom extract or powder has a statistically significant and/or greater than additive effect than: (i) sulforaphane (or a derivative thereof) alone, and/or (ii) a mushroom extract or powder alone. In some embodiments, the combination of sulforaphane and glucan has a synergistic effect compared to sulforaphane alone, and glucan alone.

In some embodiments, the combination of broccoli extract or powder and a mushroom extract or powder has a statistically significant and/or greater than additive effect than: (i) broccoli extract or powder alone, and/or (ii) a mushroom extract or powder alone. In some embodiments, the combination of broccoli extract or powder and glucan has a synergistic effect compared to broccoli extract or powder alone, and glucan alone.

The present invention provides methods of use, including methods of administration to a subject in need thereof. In some embodiments, the method comprises administration of the combination of a sulforaphane precursor, an enzyme capable of converting the sulforaphane precursor to sulforaphane, an enzyme potentiator, and a mushroom extract or powder. In some embodiments, the method comprises administration of the combination of a sulforaphane or a derivative thereof and a mushroom extract or powder. In some embodiments, the method comprises administration of the combination of a broccoli extract or powder and a mushroom extract or powder.

In some embodiments, the method relates to treating, preventing, reducing the occurrence of, decreasing the symptoms associated with, and/or reducing secondary recurrences of, cancer, in particular breast cancer, prostate cancer, colon cancer, lung cancer, liver cancer, and bladder cancer in a subject. The methods may be useful in reducing damage or slowing damage to tissues and organs, such as the breast, prostate, colon, lung, liver, and bladder. The present invention provides methods of treating, preventing, decreasing the symptoms associated with, and/or reducing secondary recurrences of diseases and conditions associated with the reproductive system (including but not limited to the breast and prostate), colon, liver, bladder, kidney, central nervous system, cardiovascular system, pulmonary system, genitourinary system, hematopoietic system, and joints. The present invention also provides for methods of treating, preventing, decreasing the symptoms associated with, and/or reducing secondary recurrences of cysts, such as benign cysts.

In some embodiments, the method relates to increasing levels or increasing gene expression of NAD(P)H:quinone oxidoreductase 1 (NQO-1) in a subject. The method may also be useful in treating, preventing, decreasing the symptoms associated with, and/or reducing secondary recurrences of diseases and conditions which would be benefited from an increase in gene expression or levels of NQO-1. Examples of such diseases and conditions include, but are not limited to cancer, myelodysplastic syndrome, cardiovascular disease, and tardive dyskinesia.

In some embodiments, the method relates to treating, preventing, reducing the occurrence of, decreasing the symptoms associated with, and/or reducing secondary recurrences of a disease or condition associated with elevated levels of quinone estrogen. Examples of such diseases or conditions include but are not limited to Examples of such diseases and conditions include, but are not limited to cancer, myelodysplastic syndrome, cardiovascular disease, and tardive dyskinesia.

In some embodiments, the methods relate to providing a beneficial effect on biomarkers, and treating, preventing, reducing the occurrence of, decreasing the symptoms associated with abnormal levels of these biomarkers. Examples of such biomarkers include, but are not limited to NADPH-dependent enzymes, thioredoxin (TXN), thioredoxin reductase-1 (Txnrd-1), glutamate-cysteine ligase subunit (GCLC), sulfotransferase 1A1 (SULT1A1), heme oxygenase-1 (HMOX1), glutathione peroxidase-3 (GPx-3), glutathione S-transferase theta 2 (GSTT2), microsomal glutathione S-transferase 1 (MGST1), aldehyde oxidase (AOX1), aldo-keto reductase 1B8 (Akr1b8), flavin-containing monooxygenase 2 (FMO2), Fc receptor region receptor III (Fcgr3), tryptase beta 1 (TPSB1), mast cell protease-6 (Mcpt6), neurexin-1-alpha (NRXN-1), microphthalmia-associated transcription factor (MITF), type II iodothyronine deiodinase (DIO2), angiopoietin-14 (Angpt14), cluster of differentiation (CD36), and Ntel. Diseases or conditions associated with elevated or abnormal levels of these biomarkers include, but are not limited to cancer, pulmonary and central nervous system tuberculosis, multiple sclerosis, Crohn's disease, atherosclerosis, osteoarthritis, asthma, stroke, emphysema, diabetic nephropathy, chronic histiocytic intervillositis of the placenta, hypertension, abdominal aortic aneurysm, inflammatory bowel disease, chronic rhinosinusitis, coronary artery disease, and kidney disease.

In some embodiments, the method comprises administering to a subject in need thereof a combination of sulforaphane and a mushroom extract or powder containing glucan. In some embodiments the method comprises administering to a subject in need thereof a combination of broccoli extract or powder and a mushroom extract or powder containing glucan. In some preferred embodiments, the method comprises administering to the subject a combination of glucoraphanin, myrosinase, ascorbic acid, and a mushroom extract or powder containing glucan. In preferred embodiments, the combinations demonstrate a synergistic effect in the methods of the present invention.

In preferred embodiments, one or more components of the combinations (for example, the sulforaphane precursor, the enzyme capable of converting the sulforaphane precursor to sulforaphane, the enzyme potentiator, the mushroom extract or powder; or the sulforaphane or derivative thereof and the mushroom extract or powder; or the broccoli extract or powder and the mushroom extract or powder) are administered together in one composition or dosage form, or separately, preferably within a period in which their therapeutic properties overlap. In some embodiments, the components of the combinations may be administered in two or more orally administrable compositions or dosage forms. For example, in some embodiments, the sulforaphane precursor, the enzyme capable of converting the sulforaphane precursor to sulforaphane, and the enzyme potentiator are administered in one orally administrable dosage form, while the a mushroom extract or powder are administered in one or more separate or additional orally administrable dosage form(s). In preferred embodiments, the components of the combination are administered in one dosage form.

In some embodiments, the combination may be administered at a frequency of 1 to 10 times daily, preferably 1 to 5 times daily, more preferably 1 to 3 times daily, and most preferably 1 time daily.

The dosages disclosed in this application refer preferably to dosages suitable for humans. Dosage calculations can be determined by those of skilled in the art by evaluating body weight, surface area, metabolic rate, and species differences.

The term "subject" refers to any animal, including mammals and birds. Mammals include, but are not limited to, humans, dogs, cats, horses, cows, camels, elephants, lions, tigers, bears, seals, and rabbits. In preferred embodiments, the subjects comprise mammals that are not consumed as food, such as humans, cats, and dogs.

EXAMPLES

Example 1 (Formulations)

The following are exemplary formulation of the present invention:
Formulation A
  Glucoraphanin-containing broccoli seed extract (about 12% w/w), 50 mg to 5 grams
  Myrosinase-containing freeze-dried broccoli sprout powder, 25 mg to 500 mg
  Ascorbic acid, 1 mg to 50 mg
  Alpha Glucan-containing shiitake mushroom extract (about 40% w/w), 1 mg to 250 mg Formulation B
  Glucoraphanin-containing broccoli seed extract (about 12% w/w), 50 mg to 5 grams
  Myrosinase-containing freeze-dried broccoli sprout powder, 25 mg to 500 mg
  Ascorbic acid, 1 mg to 50 mg
  Beta Glucan-containing maitake mushroom extract (about 20% w/w), 1 to 100 mg
Formulation C
An orally administrable composition comprising:
  Broccoli seed extract
  Broccoli sprout extract
  Maitake mushroom extract
  Ascorbic acid
  Hydroxypropylmethyl cellulose
  Microcrystalline cellulose
  Corn starch
  Ethylcellulose
  Croscarmellose sodium
  Sodium starch glycolate
  Crospovidone
  Silicon dioxide
  Sodium alginate
  Medium chain triglycerides
  Maltodextrin
  Oleic Acid
  Magnesium stearate
  Stearic acid Example 2

A Hydrophobic Interaction Chromatographic (HILIC) method was developed, comprising the following conditions:
  Column: Waters BEH Amide, 1.7-μm particle size; 2.1 mm×100 mm
  Mobile Phase: 20% 10 mM Ammonium Acetate, pH 5.0; 80% Acetonitrile;
  Separation mode: isocratic
  Column Temperature: 70° C.
  Flow Rate: 0.7 mL/min The above conditions allow separation of five typical Brassicaceae glucosinolates, including the sulforaphane precursor, glucoraphanin.

Example 3

Consumption of Glucoraphanin as a Function of the Ascorbic Acid Concentration.

About 250 mg of broccoli seed extract containing about 12% (w/w) glucoraphanin were subjected to hydrolysis by a fixed concentration of broccoli sprout-derived myrosinase in the presence of variable concentration of ascorbic acid, ranging from 0 to 600 μmoles/Liter. The reaction mixtures were thermostated at 38° C.; aliquots were withdrawn every 15 minutes for 60 minutes, and concentration of glucoraphanin determined chromatographically. The rate of glucoraphanin consumption was interpreted as the rate its conversion to sulforaphane. Graphical representation of glucoraphanin content reduction as a function of increasing ascorbic acid concentration results in a series of linear plots; the slopes of the linear regression lines reflect the rate of glucoraphanin consumption, in μmoles/minute. It is apparent that in the presence of 600 μmoles/Liter concentration of ascorbic acid, the reaction rate increased 13-fold relative to that which proceeded in the absence of modulatory effects of ascorbic acid.

| | Content of Ascorbic Acid | | | | | | |
|---|---|---|---|---|---|---|---|
| Time, min | 0 μM | 50 μM | 125 μM | 250 μM | 250 μM Filtered | 400 μM | 600 μM | |
| 0 | 93.36 | 93.36 | 93.36 | 93.36 | 93.36 | 93.36 | 93.36 | μmoles |
| 15 | 92.24 | 89.20 | 84.52 | 80.95 | 86.31 | 78.32 | 75.02 | GR |
| 30 | 90.71 | 84.24 | 75.92 | 69.06 | 79.44 | 62.78 | 55.66 | |
| 45 | 89.44 | 80.30 | 68.09 | 57.63 | 71.94 | 47.67 | 37.50 | |
| 60 | 87.79 | 76.36 | 59.41 | 45.76 | 65.18 | 33.15 | 22.09 | |
| Slope | −0.09293 | −0.28599 | −0.56217 | −0.79012 | −0.47140 | −1.00714 | −1.20029 | μmol/min |
| Intercept | 93.496 | 93.271 | 93.123 | 93.053 | 93.386 | 93.270 | 92.734 | μmol |

Example 4

Equimolar Conversion of Glucoraphanin to Sulforaphane.

A two-part experiment was conducted to further elucidate the role of ascorbic acid in modulating myrosinase activity. All solutions were prepared in 20 mM Tris-buffered saline, at pH 7.5, previously identified as an optimal for myrosinase activity; each sample tube had 100 mg of freeze-dried broccoli powder accurately weighed in as a source of myrosinase. Experiment was conducted at 38° C. for 2 hours, with sample aliquots removed in 30-minute increments, and both glucoraphanin and sulforaphane content assessed by HPLC. A strongly acidic "stop" solution was utilized to instantaneously inhibit further myrosinase activity in the removed aliquots. A control sample contained no ascorbic acid, and the enzymatic conversion proceeded unassisted by a co-factor.

PART 1. In the presence of the fixed concentration of ascorbic acid, 1 mmol/Liter, an increasing amount of broccoli seed extract (about 12% glucoraphanin, w/w) was added, ranging from 250 mg to 500 mg.

PART 2. While keeping the amount of broccoli seed extract fixed at 250 mg, the concentration of ascorbic acid was varied from 0.4 mmol/Liter to 3.8 mmol/Liter.

The table below presents glucoraphanin and sulforaphane expressed in μmoles. It is apparent that within the first 30 minutes in almost all the reaction mixtures, conversion of glucoraphanin to sulforaphane was complete. However, careful examination of the enzymatic conversion occurring in the control sample, without the stimulating effects of ascorbic acid, reveals an equimolar conversion of glucoraphanin to sulforaphane, i.e., the amount of glucoraphanin consumed results in the equivalent amount of sulforaphane produced.

| | Glucoraphanin, μmoles | | | | | Sulforaphane, μmoles | | | | |
|---|---|---|---|---|---|---|---|---|---|---|
| Time, min | 0 | 30 | 60 | 90 | 120 | 0 | 30 | 60 | 90 | 120 |
| GR 250 mg AA 0.0 mM | 58.02 | 48.57 | 37.52 | 26.58 | 15.67 | 3.42 | 12.08 | 22.27 | 33.17 | 42.89 |
| GR 250 mg AA 1.0 mM | 40.07 | | | | | 21.51 | 61.95 | 60.20 | 60.04 | 58.25 |
| GR 300 mg AA 1.0 mM | 49.31 | | | | | 24.18 | 74.40 | 73.04 | 72.19 | 70.56 |
| GR 350 mg AA 1.0 mM | 61.41 | | | | | 25.00 | 84.92 | 84.02 | 83.19 | 80.02 |
| GR 400 mg AA 1.0 mM | 71.35 | 1.56 | | | | 26.71 | 96.60 | 95.38 | 93.39 | 91.16 |
| GR 500 mg AA 1.0 mM | 89.41 | 1.01 | | | | 33.52 | 120.16 | 118.45 | 116.45 | 112.34 |
| GR 250 mg AA 0.4 mM | 45.66 | | | | | 15.98 | 62.06 | 61.01 | 60.88 | 58.90 |
| GR 250 mg AA 1.0 mM | 35.24 | | | | | 26.49 | 62.19 | 60.62 | 60.41 | 59.10 |
| GR 250 mg AA 2.0 mM | 24.94 | | | | | 36.05 | 60.85 | 59.78 | 59.65 | 58.08 |
| GR 250 mg AA 2.9 mM | 22.24 | | | | | 38.20 | 59.95 | 59.34 | 58.77 | 56.99 |
| GR 250 mg AA 3.8 mM | 21.70 | | | | | 37.87 | 58.77 | 57.79 | 58.41 | 56.17 |

In the Part 2 of the experiment, the modulatory effect of the increasing concentration of ascorbic acid on the activity of myrosinase was assessed. An initial, apparently linear, increase in myrosinase-promoted conversion of glucoraphanin to sulforaphane is observed to about 2 mmol/L of ascorbic acid concentration, followed subsequently by a considerable leveling off.

Finally, examination of sulforaphane yield of after 30 minutes within the PART 1 of the experiment, reveals that in the presence of 1 mmol/Liter of ascorbic acid, the fixed amount of myrosinase contained in 100 mg of freeze-dried broccoli sprout powder is capable of generating at least 200 μmoles of sulforaphane, in a predictably linear fashion. FIGS. 1, 2, 3, and 4 demonstrate the results of this study.

Example 5

Conversion of Glucoraphanin to Sulforaphane in the Presence of Simulated Intestinal Fluid.

Figure 4:
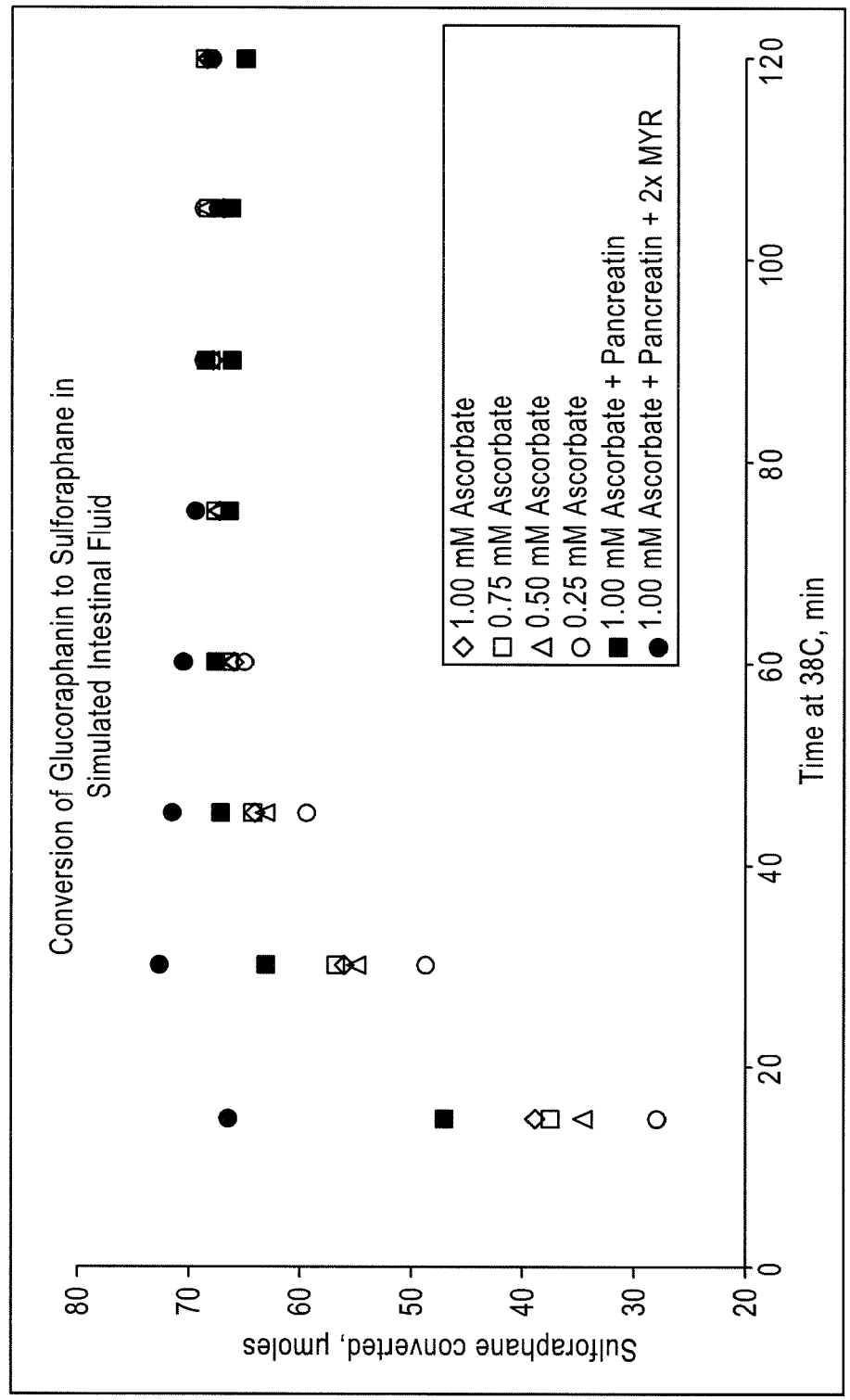
FIG. 4 is a graph showing the conversion of glucoraphanin to sulforaphane in simulated intestinal fluid, as described in Example 5.

Simulated Intestinal Fluid (SIF) powder, a commercially supplied concentrate closely approximating the human intestinal content in terms of composition, pH and ionic strength, was used. The experiment utilized a USP Dissolution Apparatus 2 (paddles), where into six dissolution vessels 500 mL of Simulated Intestinal Fluid was dispensed, along with 150 mg of freeze-dried broccoli sprout powder as a source of myrosinase. In vessels 1-4, the concentration of ascorbic acid was varied from 0.25 to 1.00 mmol/Liter; in vessel 5, in addition to 1 mmol/Liter ascorbic acid, 3.125 g of pancreatin (8×USP) was suspended; in vessel 6, in addition to 1 mmol/Liter ascorbic acid, and 3.125 g of pancreatin (8×USP), a doubled amount of freeze-dried broccoli sprout powder (300 mg) was added. After vessels were brought to 38° C., 250 mg of glucoraphanin-rich (12%, w/w) broccoli seed extract was added to each, and the resulting suspensions were stirred at 75 RPM for 2 hours. Aliquots were withdrawn every 15 minutes and assayed for sulforaphane. FIG. 4 shows direct correlation between larger yield of sulforaphane and higher concentrations of ascorbic acid, especially at the earlier stages of the experiment.

Example 6

The following study was conducted to determine the effect of the combination of sulforaphane and a maitake mushroom extract containing 20% β-glucans on gene expression of Nad(P)H:quinone oxidoreductase 1 (NQO-1). NQO-1 encodes a protein that is able to metabolize estrogen quinones, preventing them from forming DNA adducts that cause mutations and ultimately carcinogenesis. An increase in NQO-1 expression is favorable for breast, colon, liver, lung, skin and prostate health.

Figure 5:
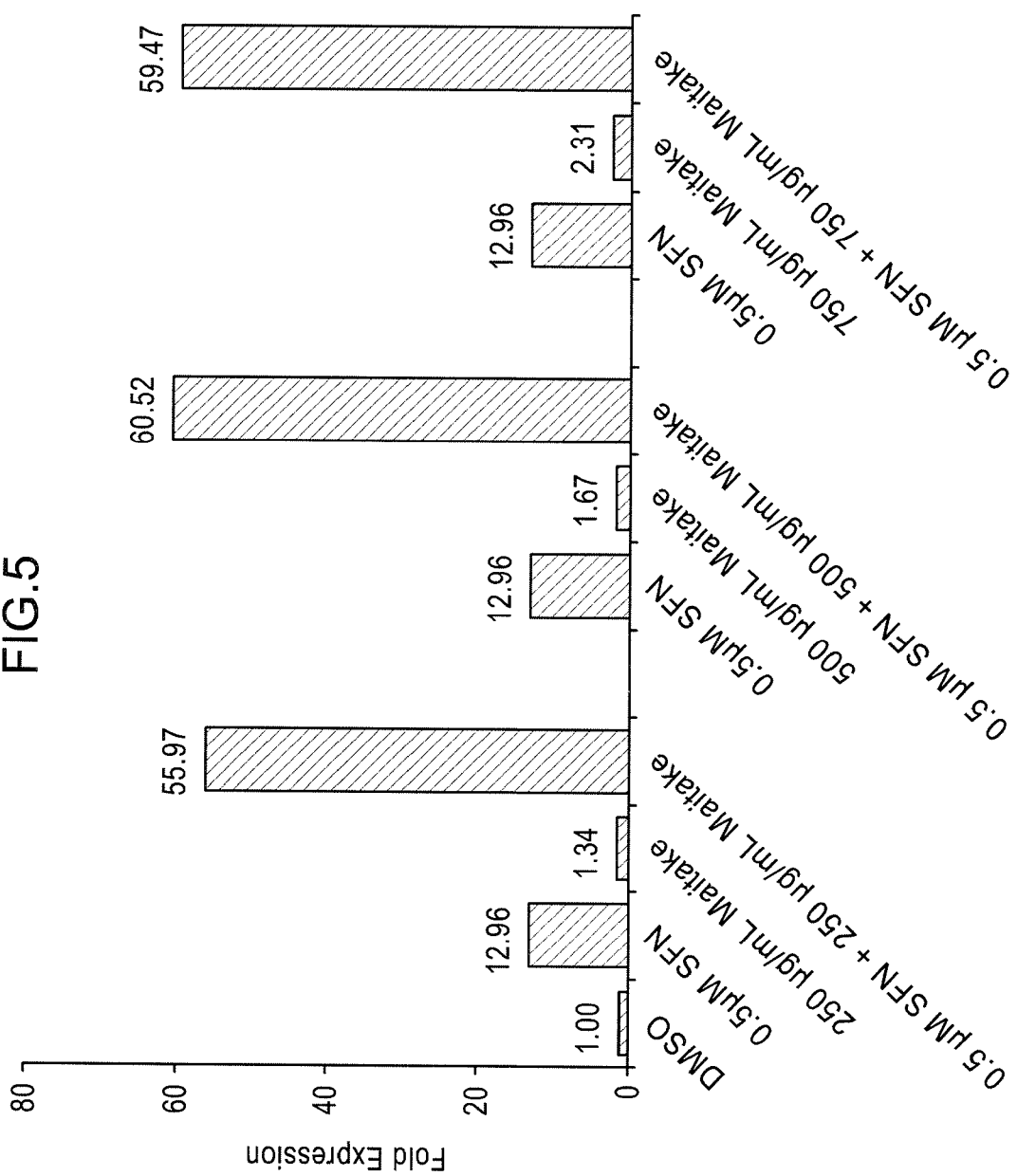
FIG. 5 is a graph showing the results of the experiment described in Example 6.

In the study, the macrophage cell line RAW 264.7 was treated with DMSO (vehicle control), sulforaphane (SFN), maitake mushroom extract having about 20% beta-glucan content (Maitake), or the combination of sulforaphane and maitake mushroom extract, for 24 hours. In particular, the cells were treated with one of the following: (i) DMSO (vehicle control), (ii) 0.5 μM SFN, (iii) 250 μg/mL Maitake, (iv) 500 μg/mL Maitake, (v) 750 μg/mL Maitake, (vi) 0.5 μM SFN and 250 μg/mL Maitake, (vii) 0.5 μM SFN and 500 μg/mL Maitake, and (viii) 0.5 μM SFN and 750 μg/mL Maitake. Gene expression of NQO-1 gene expression was analyzed via quantitative RT-PCR. The results, which are depicted in FIG. 5, show the following:

| Treatment | Fold Increase in NQO-1 gene expression |
| --- | --- |
| DMSO | 1.00 |
| 0.5 μM SFN | 12.96 |
| 250 μg/mL Maitake | 1.34 |
| 0.5 μM SFN + 250 μg/mL Maitake | 55.97 |
| 500 μg/mL Maitake | 1.67 |
| 0.5 μM SFN + 500 μg/mL Maitake | 60.52 |
| 750 μg/mL Maitake | 2.31 |
| 0.5 μM SFN + 750 μg/mL Maitake | 59.47 |

The results demonstrate that the combination of sulforaphane and maitake mushroom extract had a synergistic effect compared to each component alone. This effect was found to be more than merely additive.

Example 7

The following study was conducted to determine the effect of the combination of sulforaphane and a shiitake mushroom extract containing 40% alpha glucans on gene expression of Nad(P)H:quinonequinone oxidoreductase 1 (NQO-1).

Figure 6:
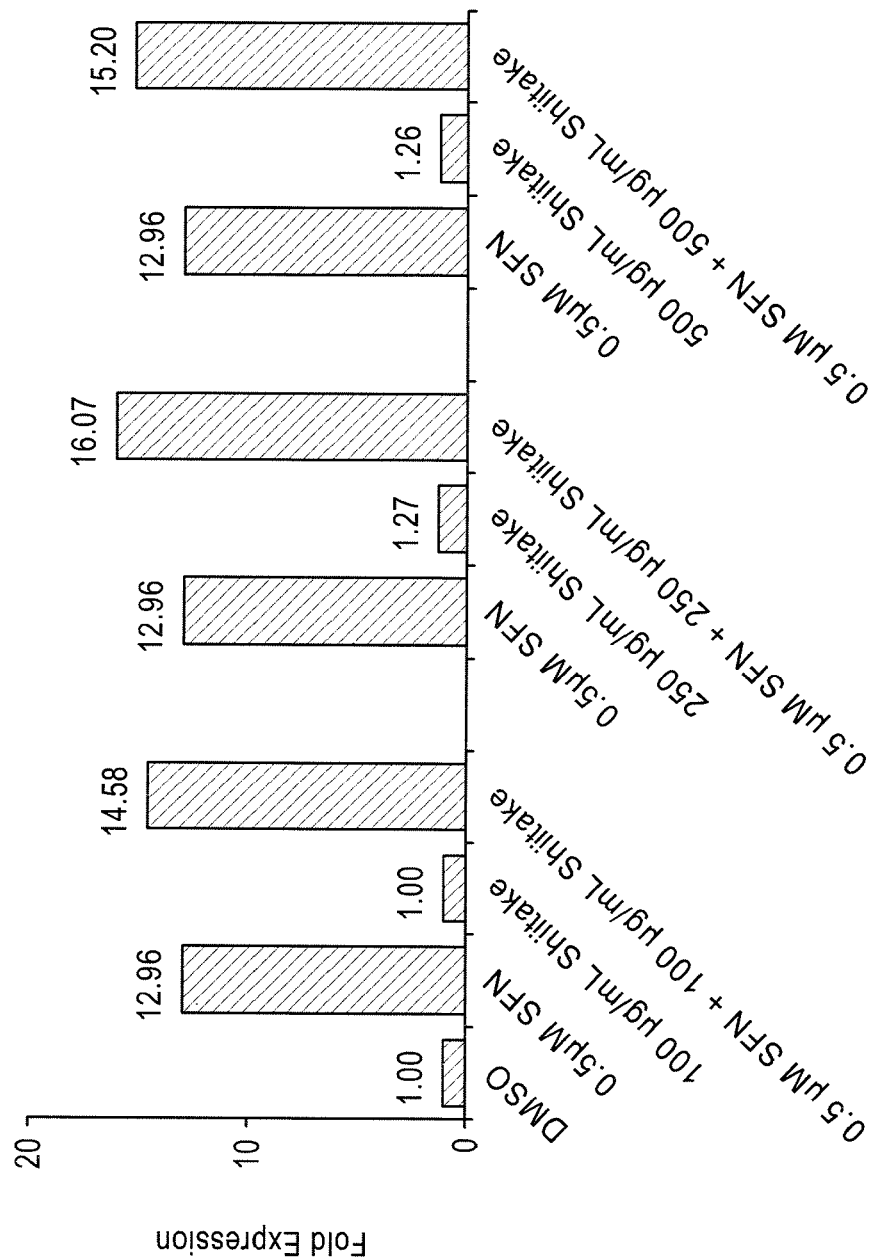
FIG. 6 is a graph showing the results of the experiment described in Example 7.

In the study, the macrophage cell line RAW 264.7 was treated with DMSO (vehicle control), sulforaphane (SFN), shiitake mushroom extract having at least 20% alpha-glucan content (Shiitake), or the combination of sulforaphane and shiitake mushroom extract, for 24 hours. In particular, the cells were treated with one of the following: (i) DMSO (vehicle control), (ii) 0.5 μM SFN, (iii) 100 μg/mL Shiitake, (iv) 250 μg/mL Shiitake, (v) 500 μg/mL Shiitake, (vi) 0.5 μM SFN and 100 μg/mL Shiitake, (vii) 0.5 μM SFN and 250 μg/mL Shiitake, and (viii) 0.5 μM SFN and 500 μg/mL Shiitake. Gene expression of NQO-1 gene expression was analyzed via quantitative RT-PCR. The results, which are depicted in FIG. 6, show the following:

| Treatment | Fold Increase in NQO-1 gene expression |
| --- | --- |
| DMSO | 1.00 |
| 0.5 μM SFN | 12.96 |
| 100 μg/mL Shiitake | 1.00 |
| 0.5 μM SFN + 100 μg/mL Shiitake | 14.58 |
| 250 μg/mL Shiitake | 1.27 |
| 0.5 μM SFN + 250 μg/mL Shiitake | 16.07 |
| 500 μg/mL Shiitake | 1.26 |
| 0.5 μM SFN + 500 μg/mL Shiitake | 15.20 |

The results demonstrate that the combination of sulforaphane and shiitake mushroom extract had a synergistic effect compared to each component alone. This effect was found to be more than merely additive.

Example 8

A subject presents with breast cancer and is suffering from symptoms including damaged breast tissue and breast pain. She is administered a tablet containing glucoraphanin, myrosinase, ascorbic acid, and a maitake mushroom extract. The tablet is an enteric coated formulation which releases the contents in the small intestine. After one month of daily administration of the tablet, the subject experiences modulation of surrogate biomarkers including NQO-1 which correlate with improved in symptoms.

Example 9

A subject presents with breast cancer and is suffering from symptoms including damaged breast tissue and breast pain. She is administered a tablet containing glucoraphanin, myrosinase, ascorbic acid, and a shiitake mushroom extract. The tablet is an enteric coated formulation which releases the contents in the small intestine. After one month of daily administration of the tablet, the subject experiences modulation of surrogate biomarkers including NQO-1 which correlate with improvement in symptoms.

What is claimed:

1. An orally administrable composition comprising a broccoli extract or powder and one or both of a maitake and a shiitake mushroom extract or powder, the broccoli extract or powder and one or both of a maitake and a shiitake mushroom extract or powder being present in amounts synergistically effective to increase levels or gene expression of NAD(P)H:quinone oxidoreductase 1 (NQO-1).

2. The orally administrable composition of claim 1, wherein the broccoli extract or powder comprises glucoraphanin in an amount of about 1 to about 75% w/w.

3. The orally administrable composition of claim 1, wherein the broccoli extract or powder comprises myrosinase.

4. The orally administrable composition of claim 1, further comprising an enzyme potentiator.

5. The orally administrable composition of claim 1, wherein the enzyme potentiator comprises ascorbic acid.

6. The orally administrable composition of claim 1, wherein the composition comprises an enteric dosage form.

7. The orally administrable composition of claim 1, comprising a maitake mushroom extract or powder comprising beta-glucan.

8. The orally administrable composition of claim 1, comprising a shiitake mushroom extract or powder comprising alpha-glucan.

9. The orally administrable composition of claim 1, comprising a maitake mushroom extract or powder and a shiitake mushroom extract or powder.

10. The orally administrable composition of claim 1, wherein the orally administrable composition is formulated to provide a synergistically effective amount of one or more glucans.

11. An orally administrable composition comprising sulforaphane or a derivative thereof and one or both of a maitake and a shiitake mushroom extract or powder, the sulforaphane or a derivative thereof and one or both of a maitake and a shiitake mushroom extract or powder being present in amounts synergistically effective to increase levels or gene expression of NAD(P)H:quinone oxidoreductase 1 (NQO-1).

12. The orally administrable composition of claim 11, comprising a maitake mushroom extract or powder comprising one or more glucans.

13. The orally administrable composition of claim 12, comprising a maitake mushroom extract or powder comprising beta-glucan.

14. The orally administrable composition of claim 11, comprising a shiitake mushroom extract or powder comprising one or more glucans.

15. The orally administrable composition of claim 14, comprising a shiitake mushroom extract or powder comprising alpha-glucan.

16. The orally administrable composition of claim 11, comprising a maitake mushroom extract or powder and a shiitake mushroom extract or powder.

17. The orally administrable composition of claim 11, further including one or more additional components selected from the group consisting of: quercetin, an aminosugar, a glycosaminoglycan, avocado/soybean unsaponifiable, a vitamin, coffee fruit, magnesium, silymarin, proanthocyanidins, ursolic acid, curcumin, phytosterols, and phytostanols.

18. The orally administrable composition of claim 11, wherein the orally administrable composition is formulated to provide a synergistically effective amount of one or more glucans.

19. An orally administrable composition comprising a source of sulforaphane and/or sulforaphane precursor and one or more glucans, the sulforaphane and/or sulforaphane precursor and one or more glucans being present in amounts synergistically effective to increase levels or gene expression of NAD(P)H:quinone oxidoreductase 1 (NQO-1).

20. The orally administrable composition of claim 19, wherein the source of sulforaphane and/or sulforaphane precursor is a vegetable of the Brassicaceae family.

21. The orally administrable composition of claim 20, wherein the source of sulforaphane and/or sulforaphane precursor is a broccoli extract or powder.

22. The orally administrable composition of claim 21, wherein the broccoli extract or powder comprises glucoraphanin in an amount of about 1 to about 75% w/w.

23. The orally administrable composition of claim 21, wherein the broccoli extract or powder comprises myrosinase.

24. The orally administrable composition of claim 21, further comprising an enzyme potentiator.

25. The orally administrable composition of claim 24, wherein the enzyme potentiator comprises ascorbic acid.

26. The orally administrable composition of claim 19, wherein the source of the one or more glucans is a mushroom or a yeast.

27. The orally administrable composition of claim 26, wherein the source of the one or more glucans is selected from one or both of a maitake and a shiitake mushroom extract or powder.

28. The orally administrable composition of claim 27, comprising a maitake mushroom extract or powder comprising beta-glucan.

29. The orally administrable composition of claim 27, comprising a shiitake mushroom extract or powder comprising alpha-glucan.

30. The orally administrable composition of claim 27, comprising a maitake mushroom extract or powder and a shiitake mushroom extract or powder.

31. The orally administrable composition of claim 26, wherein the source of the one or more glucans is a Bakers yeast comprising beta-glucan.

32. The orally administrable composition of claim 19, wherein the composition comprises an enteric dosage form.

* * * * *